US012758199B2

(12) United States Patent
Allen et al.

(10) Patent No.: US 12,758,199 B2
(45) Date of Patent: Oct. 13, 2026

(54) DEVICE AND METHOD FOR CATCHING A BIOLOGICAL SPECIMEN

(71) Applicant: Atlanta Scientific LLC, Atlanta, GA (US)

(72) Inventors: Karl Allen, Atlanta, GA (US); Patrick Strane, Atlanta, GA (US); Lei Xie, Nanjing (CN); Changqing Li, Nanjing (CN); Zhenghua Shen, Nanjing (CN); Scott Haack, Chardon, OH (US); Jiefeng Xi, Nanjing (CN); Fengxue Zhou, Nanjing (CN)

(73) Assignee: Atlanta Scientific LLC, Atlanta, GA (US)

( * ) Notice: Subject to any disclaimer, the term of this patent is extended or adjusted under 35 U.S.C. 154(b) by 1010 days.

(21) Appl. No.: 17/659,462

(22) Filed: Apr. 15, 2022

(65) Prior Publication Data

US 2022/0233179 A1 Jul. 28, 2022

Related U.S. Application Data

(63) Continuation-in-part of application No. 16/844,457, filed on Apr. 9, 2020, now abandoned.

(Continued)

(51) Int. Cl.
*A61B 10/00* (2006.01)
*B01L 3/00* (2006.01)

(52) U.S. Cl.
CPC .......... *A61B 10/0096* (2013.01); *B01L 3/502* (2013.01); *B01L 2200/141* (2013.01); *B01L 2300/0681* (2013.01); *B01L 2300/168* (2013.01)

(58) Field of Classification Search
CPC ................ A61B 10/04; A61B 10/0283; A61B 2217/005; A61B 2560/04; A61B 10/0096;
(Continued)

(56) References Cited

U.S. PATENT DOCUMENTS 4,376,053 A 3/1983 Bullock
6,905,456 B1 6/2005 Brunner
(Continued)

FOREIGN PATENT DOCUMENTS

GB 2539919 1/2017
JP 5541896 A 3/1980
(Continued)

OTHER PUBLICATIONS

International Search Report/Written Opinion released on Aug. 19, 2022 by the U.S. Patent & Trademark Office as International Search Authority for corresponding Internationl Patent Application No. PCT/US2020/027450; 12 pages.

*Primary Examiner* — Patrick Fernandes
(74) *Attorney, Agent, or Firm* — Novel IP

(57) ABSTRACT

A device and method for catching a biological specimen removed from an individual. The device includes at least an inlet channel; an outlet channel; a main chamber having an interior wall and an exterior wall, wherein the main chamber is in fluid communication with the inlet channel and is in fluid communication with the outlet channel; and a receiving structure attached to at least a portion of the interior wall or the exterior wall of the main chamber and positioned such that it does not obstruct either the inlet channel or the outlet channel, wherein the receiving structure is further configured to receive a light emitting body for illuminating the main chamber of the device before catching the biological specimen removed from an individual. The device is connected to a medical scope and a vacuum system. When the device is placed under suction, the biological specimen is (Continued)

extracted and trapped on the removable filter of the device. The removable filter is disengaged from the main chamber of the device and deposited along with the biological specimen into a specimen container.

19 Claims, 19 Drawing Sheets

Related U.S. Application Data

(60) Provisional application No. 62/854,010, filed on May 29, 2019.

(58) Field of Classification Search
CPC ...... A61B 10/0045; A61B 10/02; G01N 1/14; A61H 9/0078; A61M 1/79; A61M 1/0058; A61M 1/91
See application file for complete search history.

(56) References Cited

U.S. PATENT DOCUMENTS

| | | | | | |
|---|---|---|---|---|---|
| 7,354,410 | B2 | 4/2008 | Perry | | |
| 7,354,411 | B2 | 4/2008 | Perry | | |
| 7,591,796 | B1 | 9/2009 | Barak | | |
| 7,637,879 | B2 | 12/2009 | Barak | | |
| 7,789,246 | B1 | 9/2010 | Murphy | | |
| 7,896,825 | B2 | 3/2011 | Atkinson | | |
| 7,909,786 | B2 | 3/2011 | Bonnefin | | |
| 8,100,842 | B2 | 1/2012 | Rousso | | |
| 8,753,300 | B2 | 6/2014 | Deshpande | | |
| 8,758,282 | B2 | 6/2014 | Malhi | | |
| 8,827,936 | B1 | 9/2014 | Adaie | | |
| 9,168,197 | B2 | 10/2015 | Malhi | | |
| 9,421,142 | B2 | 8/2016 | Malhi | | |
| 9,668,932 | B2 | 6/2017 | Mansur, Jr. | | |
| 9,717,642 | B2 | 8/2017 | Deshpande | | |
| 9,839,573 | B2 | 12/2017 | Mansur, Jr. | | |
| 2007/0055188 | A1 | 3/2007 | Avni | | |
| 2007/0191731 | A1* | 8/2007 | Kaye | A61B 10/0283 | 600/565 |
| 2008/0195066 | A1* | 8/2008 | Speeg | A61B 10/0275 | 604/326 |
| 2011/0106029 | A1 | 5/2011 | Garren | | |
| 2012/0065561 | A1 | 3/2012 | Ballas | | |
| 2012/0209153 | A1 | 8/2012 | Farrow | | |
| 2013/0085429 | A1 | 4/2013 | Nelsen | | |
| 2014/0303533 | A1 | 10/2014 | Zeutzius | | |
| 2014/0323914 | A1* | 10/2014 | VanderWoude | A61B 10/0045 | 604/319 |
| 2015/0209491 | A1 | 7/2015 | Cushner | | |
| 2016/0022528 | A1 | 1/2016 | Wyatt | | |
| 2016/0361224 | A1 | 12/2016 | Ramakrishna | | |
| 2017/0160169 | A1 | 6/2017 | Bedoe | | |

FOREIGN PATENT DOCUMENTS

| | | | |
|---|---|---|---|
| JP | 2002277357 | A | 9/2002 |
| JP | 2003088491 | A | 3/2003 |
| JP | 2007209764 | A5 | 8/2007 |
| JP | 2015142761 | A | 8/2015 |
| WO | 2004041146 | | 5/2004 |
| WO | 2004075740 | A1 | 9/2004 |
| WO | 2005051250 | | 6/2005 |
| WO | 2018088892 | A1 | 5/2018 |
| WO | 2020131673 | | 6/2020 |

* cited by examiner

DEVICE AND METHOD FOR CATCHING A BIOLOGICAL SPECIMEN

CROSS-REFERENCE

The present application is a continuation-in-part application of U.S. patent application Ser. No. 16/844,457, entitled "Device and Method for Catching a Biological Specimen" and filed on Apr. 9, 2020, which, in turn, claims priority from U.S. Provisional Patent Application No. 62/854,010, of the same title and filed on May 29, 2019, both of which are hereby incorporated by reference in their entirety.

FIELD

This invention relates to a device and method for catching a biological specimen removed from an individual.

BACKGROUND

Biological specimens can be captured during surgical procedures such as laparoscopies and endoscopies. During such procedures, medical personnel will extract a biological specimen from an individual and deposit it in a container for transfer to a laboratory or separate room where further testing and study on the specimen can be performed.

Commercially available devices that are placed under suction in order to catch biological specimens typically have vacuum efficiencies below 50%. Lower vacuum performance and efficiency results in wasted energy, lower aspiration forces than expected, and potential challenges during specimen removal. In addition, many prior art devices retain bodily fluid within the device when removing the specimen from the subject. As most specimen catching devices are disposed of once done with a subject, the retained biological waste can build up in the biological waste receptacle, which can lead to contamination and potential leakage when the waste is removed from the waste receptacle.

After extracting a biological specimen using currently available commercial devices, medical personnel must deposit it into a container. Presently, during this transfer it is very likely that the specimen will be touched, accidentally or intentionally, and/or manipulated such that the specimen's integrity is harmed.

Therefore, there is a need for a device with improved performance and vacuum efficiency that can maintain a high level of suction during extraction/aspiration of a biological specimen. There is also a need for a device and method that facilitate the transfer of a biological specimen into a standard specimen container that eliminates the risk of contamination during the transfer. Further, there is an additional need for a device that removes the specimen from bodily fluid of the specimen, eliminating residual. Further, there is a need for a device and method that is minimally disruptive to the medical procedure being performed. Finally, there is a need for a device having an internal volume that can be cost-effectively illuminated, on demand, in order to assist with the visualization of the materials captured by the device.

SUMMARY

Embodiments of the present invention disclose a device for catching a biological specimen, including, but not limited to, polyps, during medical procedures including, but not limited to, colonoscopies, esophagogastroduodenoscopies, and the like. The device comprises a main chamber, a first inlet oriented on the top portion of the main chamber, a second inlet oriented on the bottom portion of the main chamber, and a removable filter configured to fit within an aperture in a side portion of the main chamber.

In some embodiments, the present specification is directed towards a device configured to catch a biological specimen removed from an individual, the device comprising at least: an inlet channel; an outlet channel; a main chamber having an interior wall and an exterior wall, wherein the main chamber is in fluid communication with the inlet channel and is in fluid communication with the outlet channel; and a receiving structure attached to at least a portion of the interior wall or the exterior wall of the main chamber and positioned such that it does not obstruct either the inlet channel or the outlet channel, wherein the receiving structure is further configured to receive a light emitting body.

Optionally, the light emitting body comprises a container with a light emitting material, wherein the container is adapted to be positioned within the receiving structure and configured to illuminate the main chamber.

Optionally, the light emitting body comprises a circuit and light emitting diode (LED), wherein the circuit and LED is configured to be positioned within the receiving structure and configured to illuminate the main chamber.

Optionally, the interior wall is at least partially curved.

Optionally, the main chamber comprises a transparent material.

Optionally, the receiving structure comprises a transparent material.

Optionally, the receiving structure is hollow having at least one side flush with the interior wall of the main chamber and a second opposing side.

Optionally, the receiving structure is cylindrical and has at least one side flush with the interior wall of the main chamber and a second opposing side.

Optionally, the second opposing side comprises an elongated opening for insertion of the container comprising the light emitting material.

Optionally, the container comprising the light emitting material is a structure that is one of cylindrical, cuboidal, and triangular prism, and has one or more dimensions dependent upon dimensions of the receiving structure.

Optionally, the receiving structure is made from clear plastic.

Optionally, a volume of the light emitting body material is in a range one of 10 cubic millimeter ($mm^3$) to 10000 $mm^3$.

Optionally, the light emitting body is adapted to be activated such that it emits light before the container is received into the receiving structure.

In some embodiments, the present specification is directed towards a method of illuminating a main chamber of a device configured to catch a biological specimen removed from an individual, the main chamber having an interior wall and an exterior wall, wherein the device comprises an inlet in fluid communication with the main chamber and an outlet in fluid communication with the main chamber, the method comprising: obtaining a volume of a light emitting material in a container; activating the light emitting material to emit light; and placing the container in a receiving structure attached to at least a portion of the main chamber such that it illuminates the main chamber before catching the biological specimen removed from an individual, wherein the receiving structure is configured to not obstruct the inlet or the outlet.

Optionally, the method further comprises inserting a filter into the main chamber, wherein the filter is adapted to collect the biological specimen.

Optionally, the method further comprises coupling the device with an endoscope and a vacuum generator adapted to apply a suction to the device.

Optionally, the main chamber comprises a transparent material.

Optionally, the receiving structure comprises a transparent material.

Optionally, the receiving structure is cylindrical and has at least one side flush with the interior wall of the main chamber and a second opposing side.

Optionally, the second opposing side comprises an elongated opening for insertion of the container comprising the light emitting material.

Optionally, the receiving structure is hollow and has at least one side flush with the interior wall of the main chamber and a second opposing side.

Optionally, the volume of the light emitting material is in a range of 10 $mm^3$ to 10000 $mm^3$.

In some embodiments, the present specification is directed towards a device configured to catch a biological specimen removed from an individual, the device comprising at least: an inlet; an outlet; a main chamber having an interior wall and an exterior wall, wherein the main chamber is in fluid communication with the inlet and is in fluid communication with the outlet; a filter positioned within the main chamber; a receiving structure attached to at least a portion of the main chamber and positioned such that it does not obstruct the inlet and does not obstruct the outlet; and a container comprising a volume of light emitting material, wherein the container is adapted to be positioned within the receiving structure and configured to illuminate the main chamber and wherein the volume of light emitting material is in a range of 10 $mm^3$ to 10000 $mm^3$.

In an aspect, the biological catching device includes a main chamber having an interior portion, a top portion, a middle portion, a bottom portion, side portions, and an aperture to receive the filter. In another aspect, the removable filter is configured to be inserted and removably retained within an aperture in the side portion of the main chamber creating a seal between the main chamber and the removable filter. The main chamber of the device can also include curved side portions made of tapered edges along the top portion and the bottom portion. In an aspect, the main chamber is made from a transparent material.

In another aspect, the removable filter includes a main body and a specimen shelf, the specimen shelf extending from the main body, wherein the specimen shelf is configured to catch the specimen while within the main chamber. In some instances, the specimen shelf is configured to fully engage inner surfaces of the interior portion of the main chamber to create a seal between the inner surfaces and the specimen shelf so that the specimen lands on the specimen shelf. In some instances, the specimen shelf further comprises pores extending through the specimen shelf to allow fluid to pass through while suction is applied. In some instances, the specimen shelf further comprises a raised edge extending upwards from a top surface of the specimen shelf, the raised edge configured to retain the specimen when removed from the main chamber. The removable filter can be made from polypropylene or plastic. In some instances, the removable filter is made from a high-contrast color material. The main body of the removable filter can include a handle portion for removing the removable filter from the main chamber. The handle portion can include tapered edges that engage corresponding tapered edges of the aperture of the side portion of the main chamber, the tapered edges forming a seal with the aperture. In other aspects, the handle portion is compressible, wherein compressed, the tapered edges disengage from the tapered edges of the aperture to easily remove the specimen filter from the main chamber.

In an aspect, the removable filter is configured to be removed from the main chamber after capturing the specimen and be transferred for testing purposes without exposing the specimen to contamination or touching. In some instances, the removable filter is configured to fit into a sampling container while still retaining the specimen, eliminating the need of transferring the specimen from the removable filter when the specimen is transported for testing.

The first inlet of the device is connected to a medical scope, such as an endoscope or colonoscope. The second inlet is connected to a vacuum system. In an aspect, the first inlet and the second inlet can be oriented diagonally from one another at opposite ends of the device, with the first inlet oriented at a corner of the top portion of the device and the second inlet oriented centrally at the bottom portion of the device. In some instances, the first inlet and the second inlet are tapered to prevent the biological specimen from becoming trapped before reaching the removable filter. In some instances, connecting joints between the first inlet and the device and the second inlet and the device include small lips to optimize seal performance.

The device is placed under suction via a suction line. A biological specimen is extracted via the working channel of the medical scope and trapped on the removable filter of the device. The removable filter containing the specimen is detached/removed from the main chamber of the device and the removable filter containing the biological specimen is deposited into a specimen container. A new removable filter is inserted into the device without disrupting the medical procedure.

The biological specimen catching device can be used by providing the device, inserting the removable filter into the main chamber, connecting a medical scope to a first inlet of the device via a first flexible tube, connecting a suction line via a second flexible tube connected to a second inlet of the device, inserting the medical scope into the individual and removing a biological specimen from the individual using the medical scope, putting the device under suction, suctioning the biological specimen and trapping it on the specimen shelf of the removable filter within the main chamber, detaching the removable filter containing the specimen from the device, and depositing the removable filter containing the specimen into a specimen container.

Further objects, features and advantages will become apparent upon consideration of the following detailed description of the invention when taken in conjunction with the drawings and the appended claims.

BRIEF DESCRIPTION OF THE DRAWINGS

The following drawings show generally, by way of example, but not by way of limitation, various examples discussed in the present disclosure. In the drawings.

DETAILED DESCRIPTION

Figure 1:
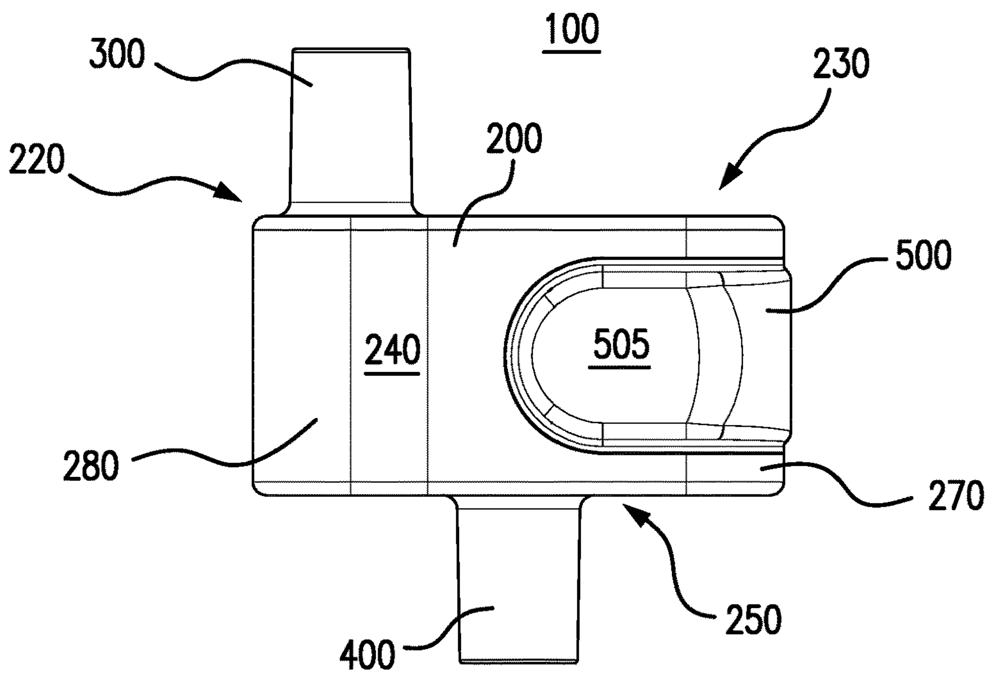
FIG. 1 is a side plan view of a device according to an embodiment of the present invention.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Embodiments of the invention will be described more fully hereinafter with reference to the accompanying drawings, in which embodiments of the invention are shown. This invention may be embodied in many different forms and should not be construed as limited to the embodiments set forth herein; rather, these embodiments are provided so that this disclosure will be thorough and complete, and will fully convey the scope of the invention to those skilled in the art.

In the description and claims of the application, each of the words “comprise” “include” and “have”, and forms thereof, are not necessarily limited to members in a list with which the words may be associated. It should be noted herein that any feature or component described in association with a specific embodiment may be used and implemented with any other embodiment unless clearly indicated otherwise.

The present invention is directed to a biological specimen catching device configured for use during medical sampling procedures. In an exemplary aspect, the biological specimen catching device is configured to be utilized with medical procedures that involve suction. The device can capture removed biological specimens, including, but not limited to, polyps. In an aspect, the medical sampling procedures can include colonoscopies, esophagogastroduodenoscopies, and any procedure in which a healthcare provider desires to retrieve a specimen smaller than the aspiration tube.

An embodiment of the device 100 is shown in FIGS. 1-7. The device 100 comprises a main chamber 200, an inlet 300, an outlet 400, and a removable filter 500, and is configured to be used with a medical scope 700 and a suction applying device 800. In an aspect, the inlet 300 is configured to be connected to a medical scope 700 and the outlet 400 is configured to be connected to a line 800 of the suction applying device (e.g., a vacuum system) (see FIG. 7). When placed under suction, the device 100 allows for the catching of a biological specimen captured using the working channel of a flexible medical scope 700 such as an endoscope or colonoscope. The device 100 is configured to be compatible with standard endoscopes, colonoscopes, and hospital vacuum systems.

FIG. 1 illustrates the device 100 with the removable filter 500 assembled with the main chamber 200. In an aspect, the main chamber 200 comprises an interior portion 210, an exterior portion 220, a top portion 230, a middle portion 240, a bottom portion 250, an aperture 290, an aperture side portion 270, and a non-aperture side portion 280. The side portion 270 of the main chamber 200 and the removable filter 500 are curved, providing superior ergonomics and ensuring ease of manipulation by the end user. Ergonomics/workflow are maximized as the removable filter 500 can be very easily observed and removed/detached from the device 100.

In an aspect, the removable filter 500 is configured for a single use, with multiple removable filters 500 being available for use with the chamber 200. That is, once a specimen has been captured on the removable filter 500, it can be removed and placed into a specimen container, with a new removable filter 500 placed within the chamber 200 for use during the collection process. In addition, new removable filters 500 can be easily and quickly re-inserted into the aperture 290 of the main chamber 200 to minimize the down time between aspirations, as the removal of a filter 500 leads to the loss of aspiration pressure as suction is applied. Additionally, the dimensions of the removable filter 500 allow the medical professional manipulating the biological specimen to minimize the transfer time to the specimen container, with the removable filter 500, while retaining the specimen, is configured to be received within the container.

In an aspect, the main chamber 200 of the device 100 is made from a transparent material, including, but not limited to, clear plastic. In other aspects, other transparent materials can be utilized. While non-transparent materials can be used, it is preferable to use a transparent material in order to see when a biological sample has entered the main chamber 200 and is trapped on the removable filter 500, discussed below. The main chamber 200 is tapered/rounded along its edges between the top portion 230 and bottom portion 250. In an aspect, the top portions 230 and the bottom portions 250 have equal heights to improve the ergonomics of the chamber 200. In an exemplary aspect, the main chamber includes a middle portion 240 that is tapered/rounded along the aperture side and non-aperture side portions 270, 280. The tapered nature of the side portions 270, 280 along the middle portion 240 prevents user injury from the exterior surface 220 while reducing the resistance to flow within the interior portion 210 during aspiration and the likelihood of damage to the specimen during extraction/aspiration.

Figure 2:
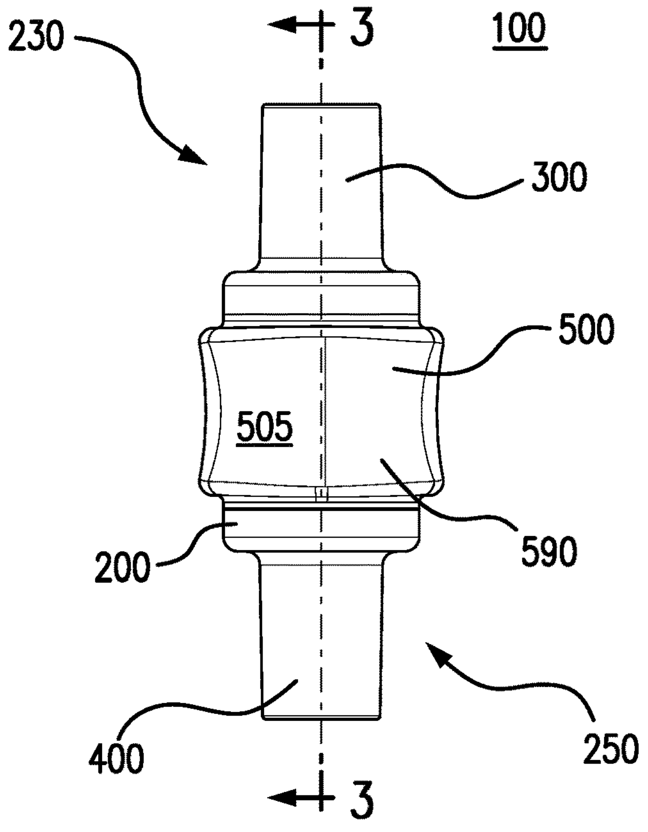
FIG. 2 is a front plan view of the device of FIG. 1.

The first and second inlets 300, 400 extend from the top portion 230 and the bottom portion 250 of the chamber 200 respectively, as shown in FIG. 2. In an aspect, the inlet 300 and the outlet 400 are tubular extensions in communication with the interior portion 210 of the main chamber 200. The inlet 300 and the outlet 400 provide a continuous pathway from the subject via the endoscopic tool 700 and a suction-applying device 800 through the chamber 200 (see FIG. 7). In an aspect, the inlet 300 and the outlet 400 are identical. In an exemplary aspect, the inlet 300 and outlet 400 measure 12 mm vertically with a diameter of 8.39 mm. While the dimensions of the inlet 300 and outlet 400 can vary from those discussed above, these dimensions allow for free airflow during aspiration and ensure compatibility with standard tubing/connectors.

The inlet 300 is oriented on the top portion 230 of the main chamber 200 of the device 100 and the outlet 400 is oriented on the bottom portion 250 of the main chamber 200 of the device 100. In an aspect, the inlet 300 and outlet 400 are oriented in a diagonal fashion; i.e., not in direct alignment with one another. This orientation allows for maximal viewing of the collected specimen, as well as for maximum visibility of the removable filter 500. The relative locations of the inlet 300 and outlet 400 also aid in the separation/removal of bodily fluid and bioburden from the biological sample. In an embodiment, the inlet 300 is oriented on the non-aperture side 280 of the main chamber 200 and the outlet 400 is oriented in the middle of the bottom portion 250 of the main chamber 200. While it is possible for the outlet 400 to be arranged closer to the aperture side 270, pooling can occur directly under the filter 500, which makes collection of the specimen more challenging. The alignment of the outlet 400 not directly below the filter 500 and not directly below the inlet 300 minimizes the possibility of fluid pooling within the device 100 and optimizes drainage. In addition, the offset alignment of the inlet 300 and the outlet 400 increase the ergonomics of the device 100, improving the handling of the device 100 by the clinician. In an aspect, the main chamber 200, the inlet 300, and the outlet 400 include an internal taper 310 that prevents the specimen from becoming trapped before reaching the removable filter 500.

Figure 3:
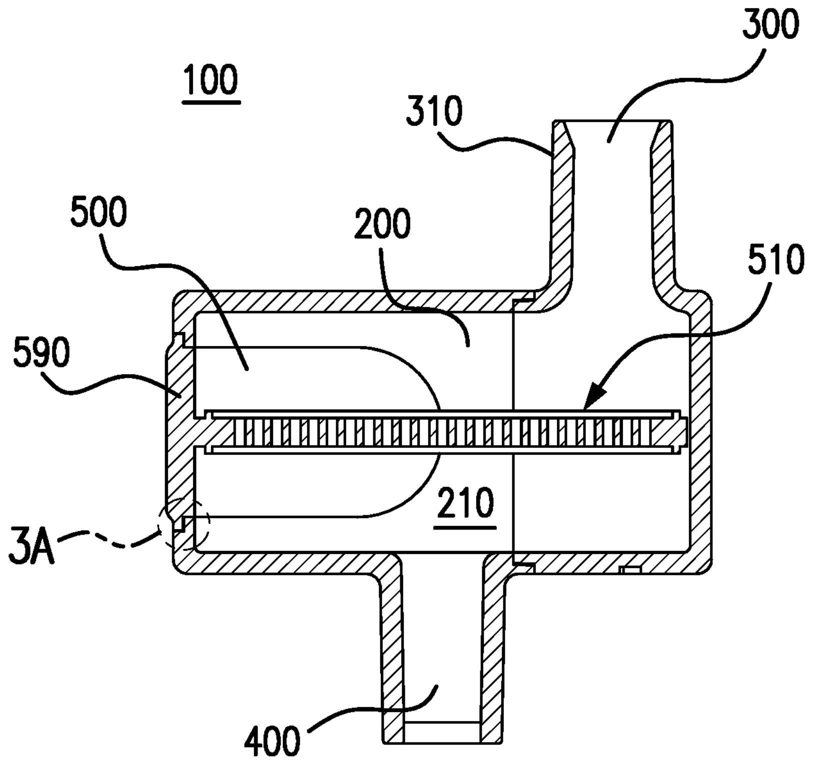
FIG. 3 is a side section view of the device of FIG. 1.

FIG. 3 is a side section view of the device 100 showing the removable filter 500 within the main chamber 200 of the device 100. The removable filter 500 includes a main body 505 and a specimen shelf 510 with a top surface 530 and a bottom surface 540. The specimen shelf 510 includes pores 550 (see FIG. 5). The main body 505 includes a handle portion 590 for the removable filter 500. The edges of the handle portion 590 comprise tapered edges/grooves 595 that intersect with corresponding raised edges/grooves 570 of the specimen shelf 510. In an aspect, the shelf 510 is positioned in the center of the main body 505 of the filter 500. In such aspects, the raised edges/grooves 570 of the specimen shelf 510 are found surrounding the top surface 530 and bottom surface 540. By positioning the shelf 510 in the middle of the main body 505, and also the edges 570 on both sides, the filter 500 can be inserted in two different vertical orientations and still function correctly. That is, the filter 500 is reversible in the vertical orientation, with the filter 500 being able to be inserted with the top surface 530 oriented upwards one way, and the bottom surface 540 being oriented upwards the other way. This increases in the efficiency of replacing the filter 500 as the clinician does not need to be worried about the correct vertical orientation.

Figure 3A:
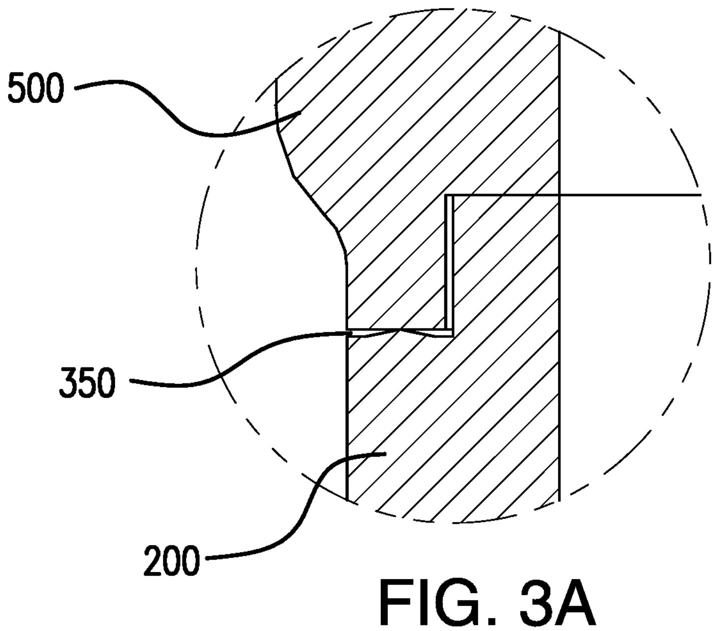
FIG. 3A is a section detail of FIG. 3 showing the corresponding edges of the removable filter and the main chamber of the device of FIG. 1.

FIG. 3A is a section detail of FIG. 3 showing the corresponding edges of the removable filter 500 and the main chamber 200 of the device. As shown in FIGS. 3-3A, the tapered edges 595 of the handle portion 590 correspond to matching step/grooves 295 found along the aperture 290 of the main chamber 200 that form a lip/groove feature 350 when the removable filter 500 is inserted into the main chamber 200. The combination of the tapered edges 595 with the lip 295 of the aperture form a sealed unit when the removable filter 500 is inserted into the main chamber 200 of the device 100 improving the vacuum efficiency by increasing the quality of the seal between the chamber 200 and the removable filter 500.

Figure 4:
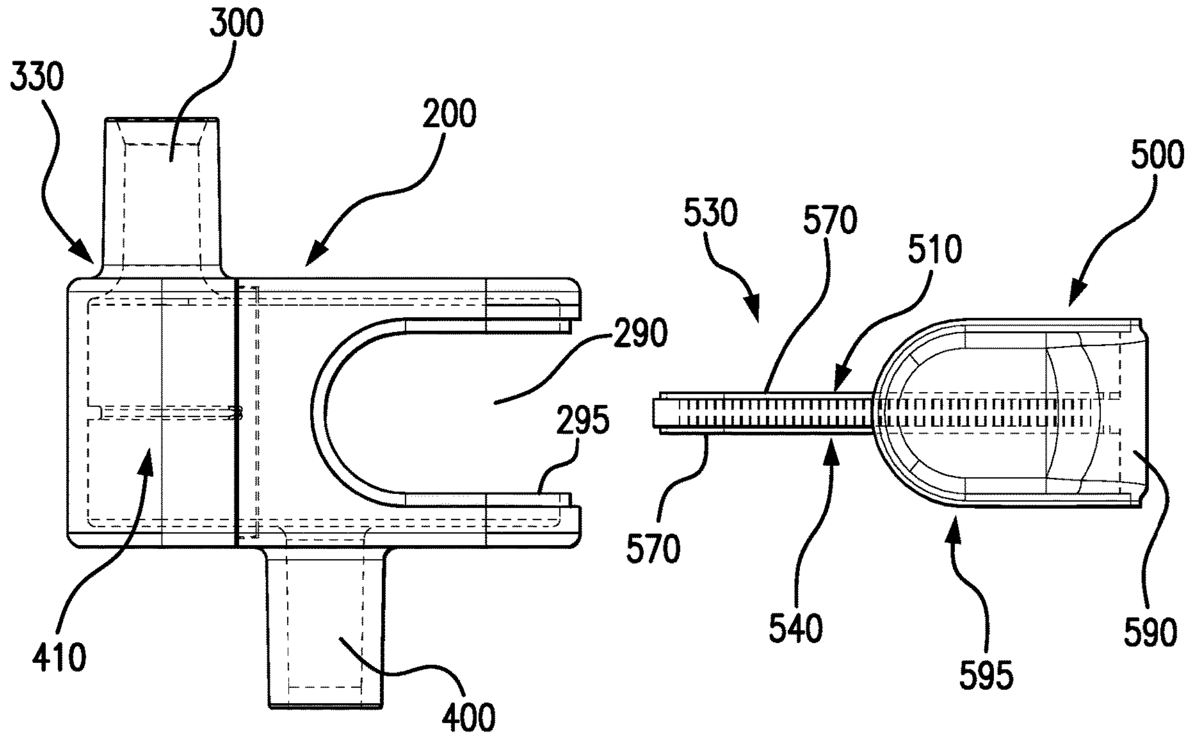
FIG. 4 is a side section view of the device of FIG. 1 showing the main chamber separated from the removable filter.
Figure 5:
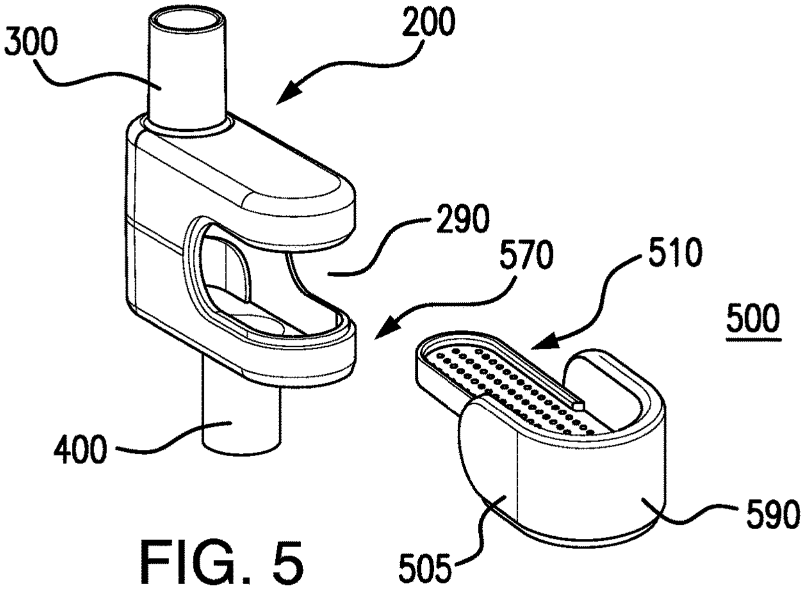
FIG. 5 is a perspective view of the device of FIG. 1 showing the main chamber separated from the removable filter.

Referring to FIGS. 4-5, the length and width of the specimen shelf 510, including its curved edges, are configured to match the dimensions of the interior portion 210 of the main chamber 200 along the middle portion 240, to help form a seal. The raised edge 570 of the specimen shelf 510 extends upwards from the top surface 530 and aids in the retention of the specimen on the specimen shelf 510 after the specimen has been removed from the subject, traveled into the inlet 300, traveled into the main chamber 200 and is caught/trapped. In addition, the matching dimensions of the interior 210 and the shelf 510, and the raised edge 570 ensure that the flow of the fluid travels through the pores 550 of the specimen shelf 510, and not around the shelf 510. The handle portion 590 is used to disengage the removable filter 500 from the main chamber 200 of the device 100 before the removable filter is deposited into a specimen container.

FIGS. 4-5 show the removable filter 500 separated/disengaged from the main chamber 200 of the device. The removable filter 500 is configured to fit into and be inserted and removed within the aperture 290 in the aperture side portion 270 of the main chamber 200. The main body 505 of the removable filter 500 serves as a handle portion 590 for removing/disengaging the removable filter 500 from the main chamber 200. In an aspect, the handle portion 590 of the removable filter 500 has tapered/curved edges 595 that correspond with the tapered/curved edges 295 of the aperture side portion 270. This provides a seal when the removable filter 500 is inserted into the aperture 290 of the aperture side portion 270 of the main chamber 200 and makes it easy to manipulate the device 100. In an aspect, when the handle portion 590 of the removable filter 500 is compressed, the tapered edges 595 disengage from the corresponding tapered edges 295 of the aperture 290 to easily disengage the removable filter 500 from the main chamber 200.

Figure 7:
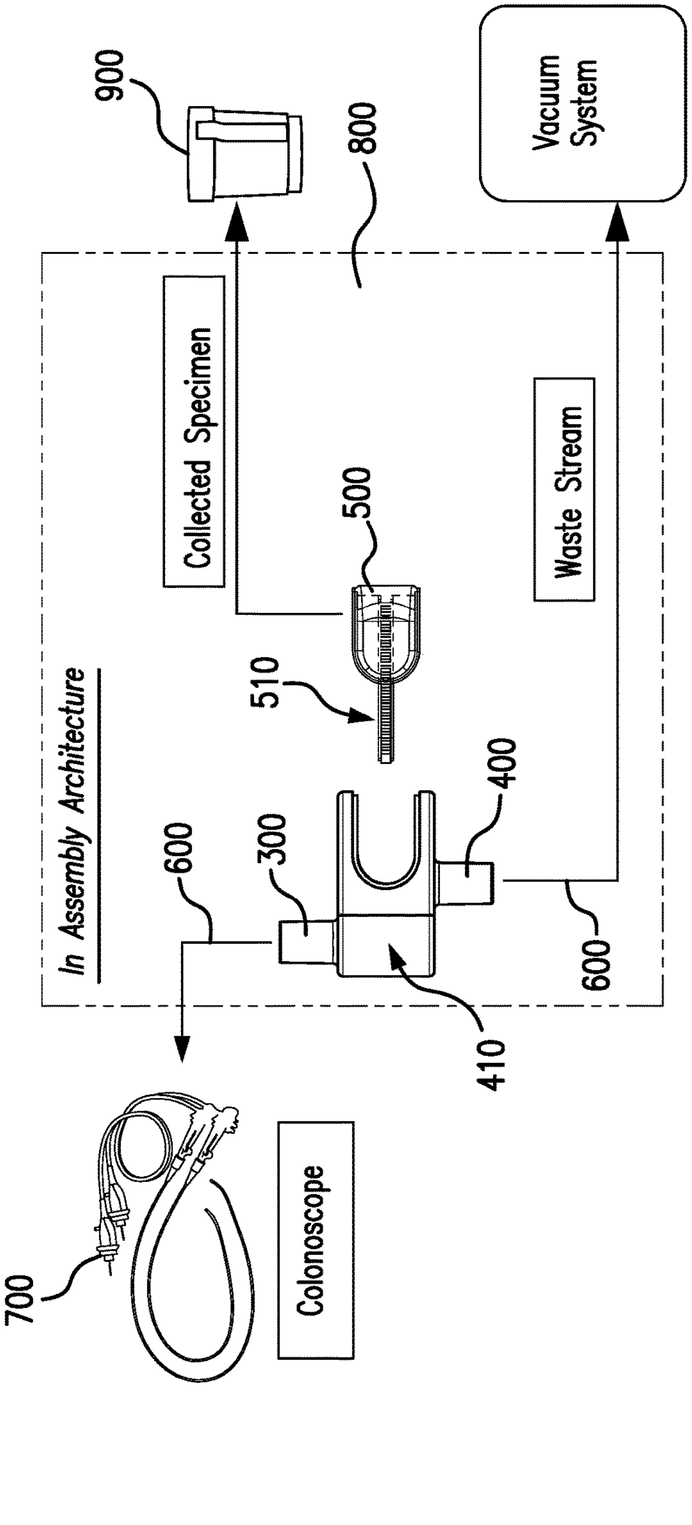
FIG. 7 is a schematic incorporating the device of FIG. 1 showing how it is connected to other aspects of the present invention during use.

The removable filter 500 is configured to fit into the main chamber 200 in between the first inlet 300 and the second inlet 400 in between the fluid pathway from the endoscope 700 and the vacuum 800 (see FIG. 7). The removable filter 500 is configured to be inserted and removably retained within the aperture 290 in the side portion 270 of the main chamber 200 creating a seal between the main chamber 200 and the removable filter 500. The biological specimen is extracted from the individual and trapped on the removable filter 500 while the device 100 is placed under suction.

In an aspect, both the main chamber 200 and the removable filter 500 of the device 100 are made from polypropylene material, which provides a better seal between the removable filter 500 and the main chamber 200 of the device 100 when in use. In an aspect, the removable filter 500 is made from plastic or a similar high-contrast material such as ABS, polypropylene and polycarbonate, to allow for easy viewing of the trapped biological specimen within the device 100 and to maximize compatibility with specimen containers 900. In a preferred embodiment, the removable filter 500 is dimensioned to fit entirely within an average sized specimen container 900. In an aspect, such specimen containers 900 can have dimensions that are approximately 45 mm in diameter and 50 mm in height. However, the dimensions can vary.

In an aspect, the main chamber 200 includes a support shelf 410 such that the filter 500 is supported during use whereon the specimen shelf 510 of the removable filter 500 abuts when inserted, ensuring a secure fit and tight seal. In other embodiments, the chamber 200 does not have a shelf 410. The connecting joints 330 (see FIG. 4) between the inlets 300, 400 and the main chamber 200 include small lips to optimize seal performance.

Figure 6:
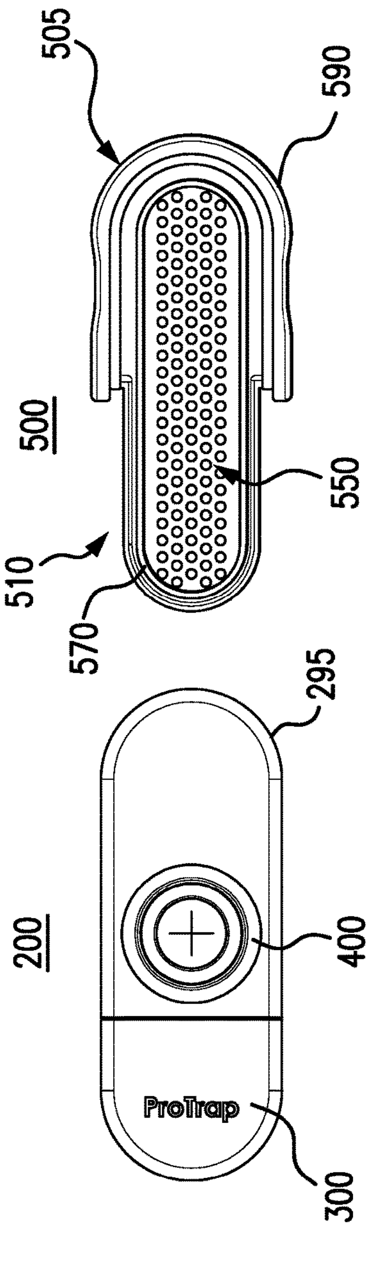
FIG. 6 is a top section view of the device of FIG. 1 showing the main chamber separated from the removable filter.

FIG. 6 is a top section view of the device showing the removable filter 500 separated from the main chamber 200 of the device 100. The top surface 530 of the specimen shelf 510 of the removable filter 500 comprises small pores 550 disposed along the top surface 530 of the specimen shelf 510 that allow fluid to pass through when the device 100 is under suction. In an exemplary aspect, each pore 550 has a diameter of approximately 0.75 mm and the pores 550 are spaced approximately 1.3 mm from one another. The pores 550 can take various forms, as well as different geometrical patterns. In an aspect, the pores 550 can have hexagonal, square, or rectangular symmetry. In an aspect, the pores 550 take up approximately 15.5% of the available surface area on the specimen shelf. The spacing of the pores 550 allows the device 100 to maintain high suction when in use while maintaining the appropriate pore size for specimen collection. The spacing and the size of the pores 550 can vary in other embodiments. In other aspects, the pores 550 can take up between 5% to 25% of the surface area of the specimen shelf. Regardless of the different dimensions, the pores 550 should be of a size that allow fluid to travel through and maintain high suction while preventing a specimen from traveling through a pore 550.

FIG. 7 is a schematic representation of the assembly according to an aspect of the present invention. The inlet 300 of the device 100 is connected to a medical scope 700 such as a colonoscope, endoscope or the like via a flexible tube 600. The outlet 400 of the device 100 is connected to a suction line/vacuum system 800 with another flexible tube 600. The flexible tube 600 is made from silicon or like material. The medical scope 700 is inserted into an individual during a surgical procedure such as an endoscopy or laparoscopy. The assembly comprising the medical scope 700 and device 100 is placed under suction using the vacuum system 800. The medical scope 700 is used to isolate/remove the desired biological specimen from the individual. The biological specimen is then suctioned through the first inlet 300, landing on the specimen shelf 510 of the removable filter 500 within the main chamber 200 of the device 100. The removable filter 500 is then detached from the main chamber 200 of the device 100 and the removable filter containing the specimen is deposited into a specimen container 900. The removable filter 500 is replaced with a new/unused removable filter 500 and additional biological specimens can be extracted and deposited as required.

In an exemplary aspect, when the removable filter 500 is inserted into the main chamber 200, this assembly measures 38 mm horizontally and 20 mm vertically. The dimensions of the device 100 and removable filter 500 allow for the removable filter 500 to be entirely deposited into a specimen container. However, the device 100 and its components are not limited to such dimension, and in other aspects, the dimensions can vary. However, in most aspects, the device 100 and the removable filter 500 have dimensions that allow the removable filter 500 to fit into a specimen container 900 while still maintaining a high suction efficiency when inserted into the main chamber 200.

Figure 8A:
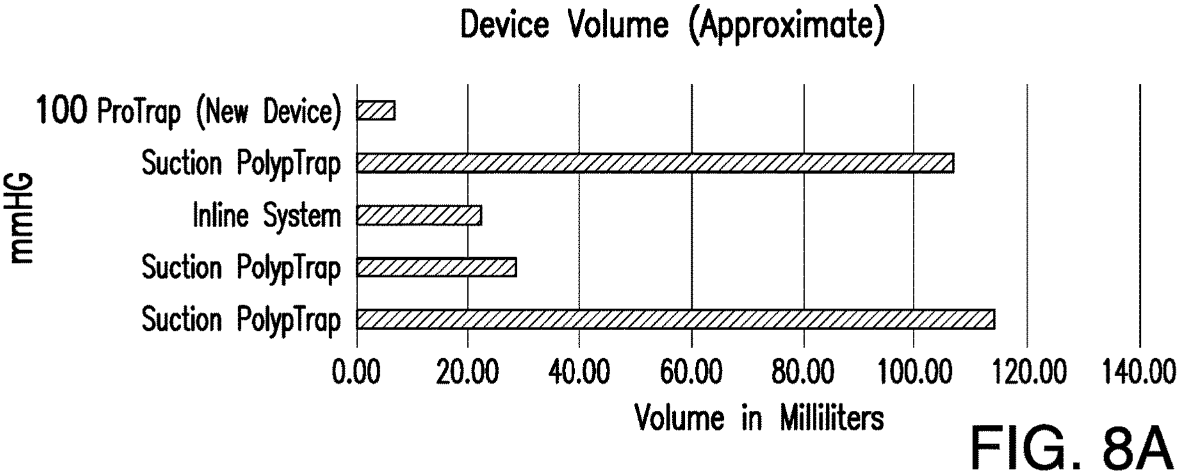
FIG. 8A is a graph showing the performance of the device of FIG. 1 in comparison to commercially available devices.

The composition of the device 100 as discussed above has been shown to have benefits over other commercially available products. As shown in FIG. 8A, the device 100 volume is approximately 400% smaller than the smallest commercially available device on the market. The small, compact size of the device 100 makes the device 100 easy for the user to manipulate use, as well as remove and reinsert removable filters 500 during a medical procedure. The size also ensures that the removable filter 500 and its contents can be deposited entirely into a specimen container.

Figure 8B:
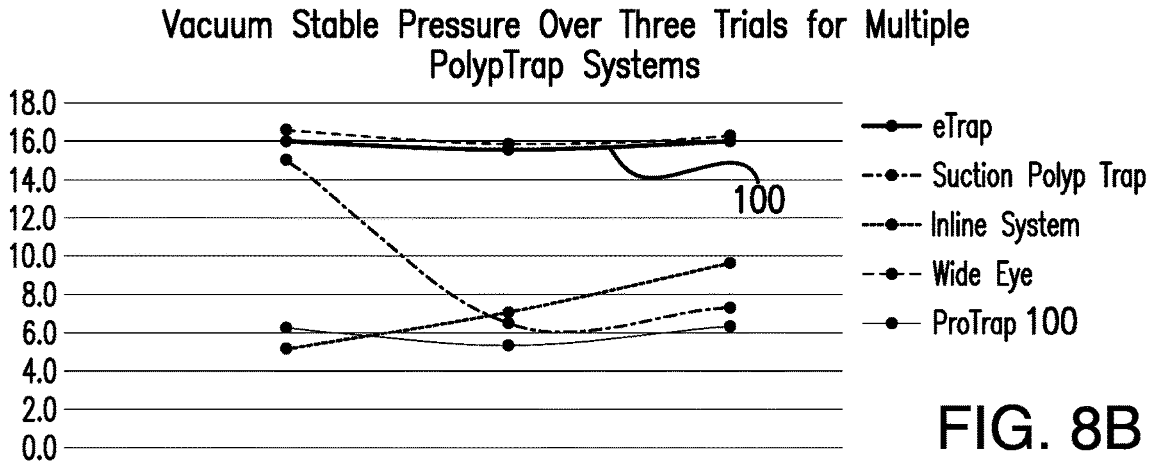
FIG. 8B is another graph showing the performance of the device of FIG. 1 in comparison to commercially available devices.

FIG. 8B shows the vacuum pressure of the device 100 over multiple trials in comparison to commercially available devices. The device 100 exhibits stable pressure over three trials and provides a more consistent performance profile with less variation than other solutions. By employing a closed system featuring optimized seals and ergonomics including the external curvature of the main chamber 200 and removable filter 500, the device 100 is able to maintain stable pressure over multiple uses.

Figure 8C:
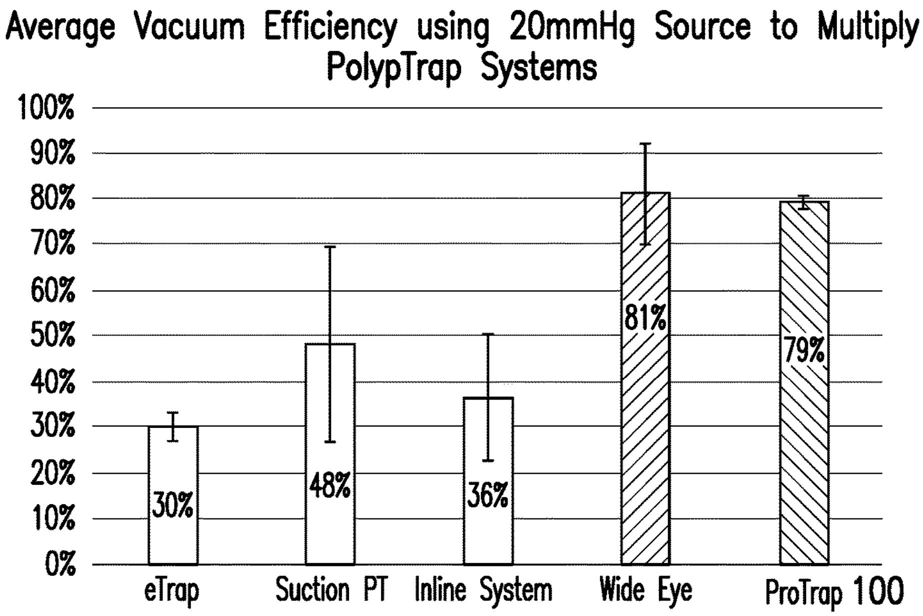
FIG. 8C is another graph showing the performance of the device of FIG. 1 in comparison to commercially available devices.

FIG. 8C shows the average vacuum efficiency of the device 100 in comparison to commercially available devices using a 20 inHg/67.7 kPa vacuum source (within range of standard hospital vacuum systems). The device 100 exhibits less variation in its efficiency than any other device. The alternative devices are unable to maintain vacuum efficiency effectively after the being opened/used once and are therefore not ideal for insertion and removal of a removable filter 500 repeatedly during a medical procedure. No commercially available device offers all of the advantages of the present device 100 which include being small enough for easy manipulation, having a removable filter that fits entirely within a specimen container while also maintaining vacuum efficiency and pressure over multiple uses.

In an optional embodiment, the biological specimen receiving device, also termed as specimen container 900, of the present specification is designed to include a receiving structure positioned within, and internal to, the main chamber of the device. A container comprising a luminescent or glow material may be placed within the receiving structure to illuminate the internal chamber or volume of the device, thereby enabling a specimen placed in a filter, as described above, in the main chamber to be seen clearly via an endoscopic device. In one embodiment, the main chamber of the device comprises polyethylene terephthalate, polycarbonate, or any other transparent material. The filter may be comprised of thermoplastic elastomer, thermoplastic polyurethane, silicone or other flexible material. Finally, the luminescent material is chosen to meet biological safety and/or regulatory requirements.

Figure 9A:
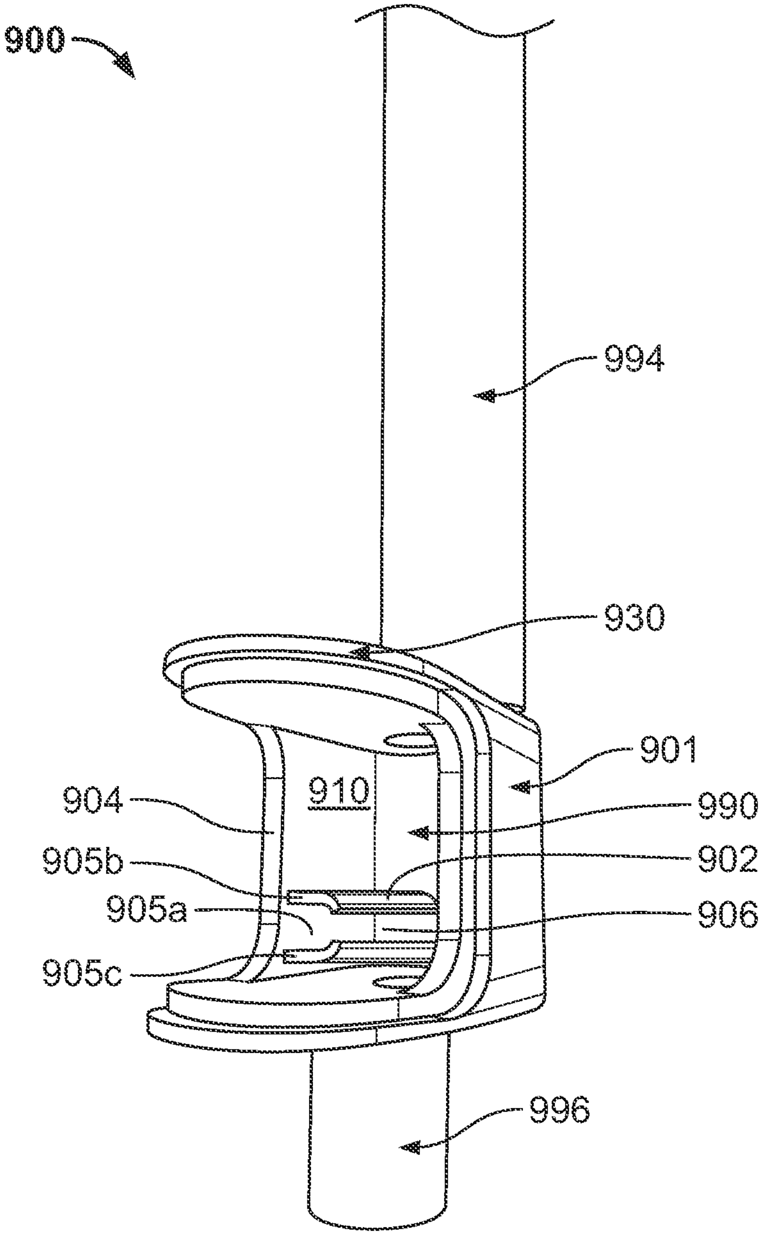
FIG. 9A is an illustration of a receiving structure coupled with an internal wall of a biological specimen receiving device, in accordance with an embodiment of the present specification.
Figure 9B:
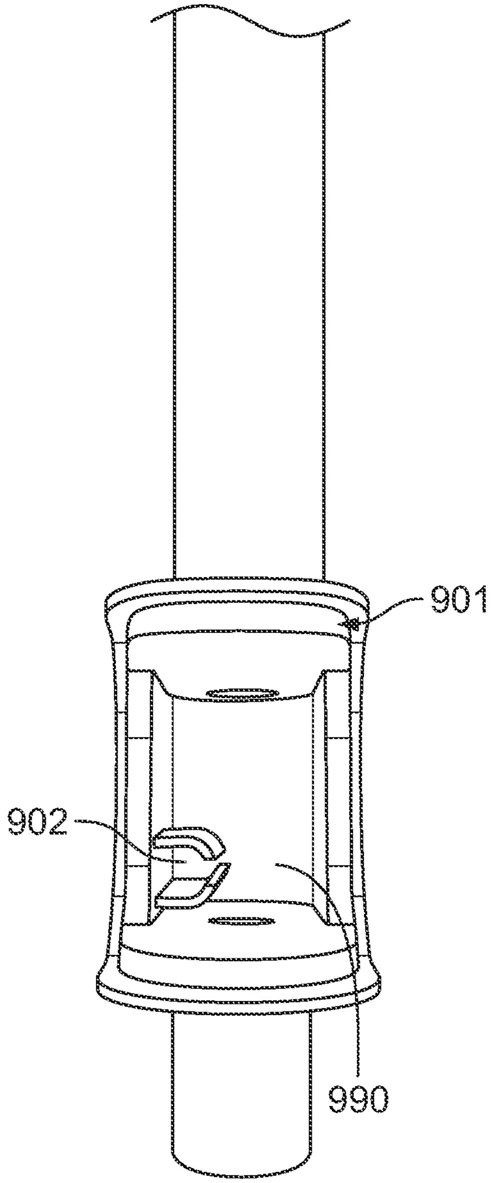
FIG. 9B illustrates a front view of the receiving structure shown in FIG. 9A, in accordance with an embodiment of the present specification.
Figure 9C:
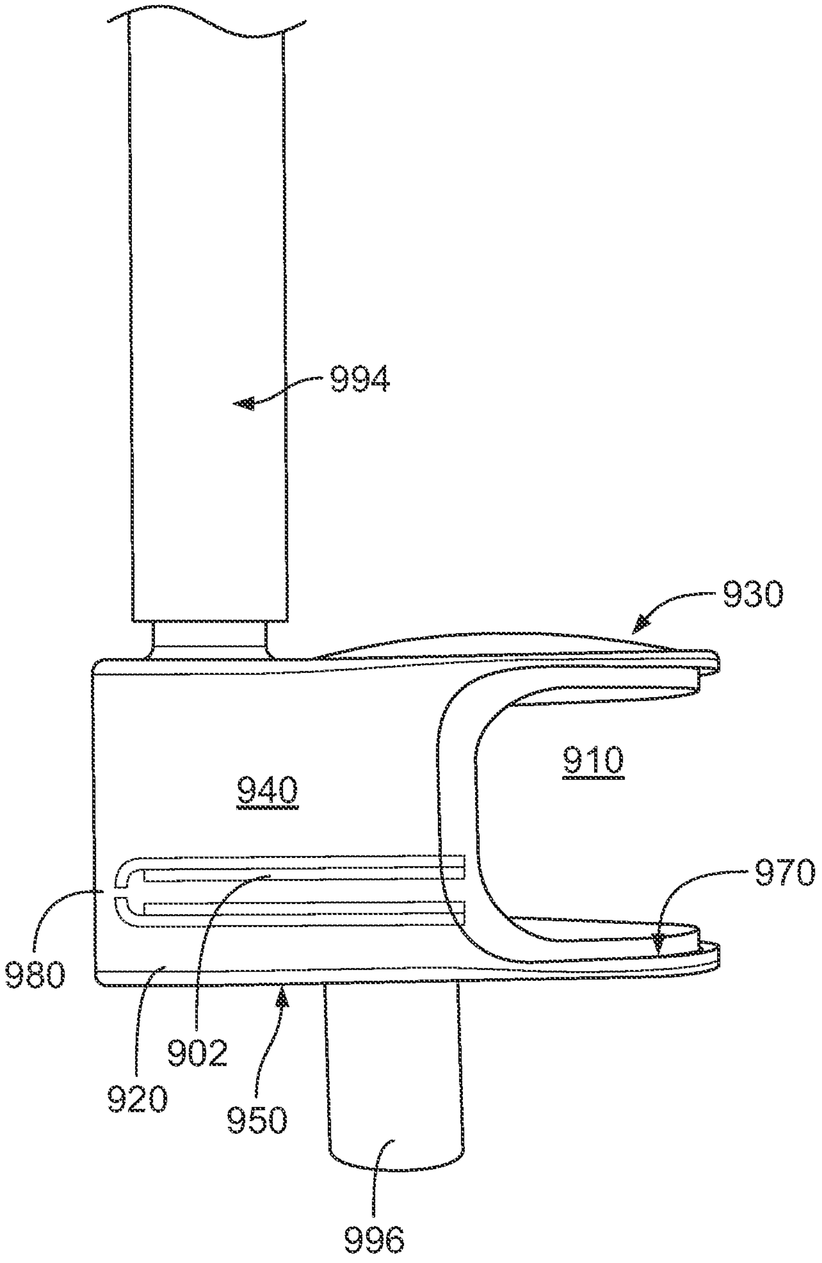
FIG. 9C illustrates a side view of the receiving structure shown in FIG. 9A, in accordance with an embodiment of the present specification.

FIG. 9A illustrates a receiving structure 902 coupled with an internal wall of a main chamber 901 of a specimen container 900, in accordance with an embodiment of the present specification. Specimen container 900 is configured to receive a biological specimen in a main chamber 901 of the container 900. FIG. 9B illustrates a front view of the receiving structure 902 shown in FIG. 9A, in accordance with an embodiment of the present specification. FIG. 9C illustrates a side view of the receiving structure 902 shown in FIG. 9A, in accordance with an embodiment of the present specification. In one embodiment, the receiving structure 902 is molded into, or onto, a surface of the internal walls of the interior portion 910 of main chamber of specimen container 900. In another embodiment, the receiving structure 902 is welded, glued, or clipped into, or onto, a surface of the interior portion 910 of main chamber of specimen container 900. In embodiments, the receiving structure 902 may be of any shape that is capable of mating with, and snapping into, the main chamber 901 of the specimen container 900.

In an aspect, receiving structure 902 of the specimen container 900 is made from a transparent material, including, but not limited to, clear plastic, and is the same material as the main chamber 901. In other aspects, other transparent materials can be utilized. While non-transparent materials can be used, it is preferable to use a transparent material in order to see when a biological sample has entered the main chamber 901 and is trapped on the removable filter, which has been discussed in detail above.

Referring to FIGS. 9A, 9B and 9C, in an aspect, the main chamber 901 comprises an interior portion 910 (210 in FIG. 1), an exterior portion 920 (220 in FIG. 1), a top portion 930 (230 in FIG. 1), a middle portion 940 (240 in FIG. 1), a bottom portion 950 (250 in FIG. 1), an aperture 990 (290 in FIG. 1), an aperture side portion 970 (270 in FIG. 1), and a non-aperture side portion 980 (280 in FIG. 1). The side portion 970 of the specimen container 900 is curved, providing superior ergonomics and ensuring ease of manipulation by the end user.

The main chamber 901 is tapered/rounded along its edges between the top portion 930 and bottom portion 950. In an aspect, the top portions 930 and the bottom portions 950 have equal heights to improve the ergonomics of the chamber 901. In an exemplary aspect, the main chamber includes a middle portion 940 that is tapered/rounded along the aperture side and non-aperture side portions 970, 980. The first and second inlets 994, 996 extend from the top portion 930 and the bottom portion 950 of the chamber 901 respectively (shown in FIG. 9A). In an aspect, the first inlet 994 and the second inlet (outlet) 996 are tubular extensions in communication with the interior portion 910 of the main chamber 901. Specifically, inlet 994 is oriented on the top portion 930 of the main chamber 901 of the specimen container 900 and the second inlet (outlet) 996 is oriented on the bottom portion 950 of the main chamber 901 of the specimen container 900. In an embodiment, the inlet 994 is oriented on the non-aperture side 980 of the main chamber 901 and the second inlet (outlet) 996 is oriented in the middle of the bottom portion 950 of the main chamber 901. The removable filter (shown in FIGS. 1-7) is configured to fit into the main chamber 901 in between the first inlet 994 and the second inlet 996 in between the fluid pathway from the endoscope and the vacuum (see FIG. 7). The removable filter is configured to be inserted and removably retained within the aperture 990 in the side portion 970 of the main chamber of specimen container 900 creating a seal between the main chamber of specimen container 900 and the removable filter. In embodiments, the receiving structure 902 comprises a first elongated wall 905*a* encasing the internal hollow space, wherein the first wall 905*a* is connected to and abuts internal wall 904 of the main chamber 901 of specimen container 900. Receiving structure also comprises a second elongated wall 905*b*, which is connected to a top portion of first elongated wall 905*a* and a third elongated wall 905*c*, which is connected to a bottom portion of first elongated wall 905*a*. Second elongated wall 905*b* and third elongated wall 905*c* are curved toward each other to form an opening/slot 906 extending throughout a length of the receiving structure 902 as shown in FIG. 9A.

In embodiments, the receiving structure 902 is positioned toward the bottom portion 950 of main chamber 901, and close to inlet 996, which is oriented in the middle of the bottom portion 950 of main chamber 901. Thus, the receiving structure 902 is positioned such that it does not interfere with the insertion of the removable filter. Receiving structure 902 is configured to position at least one lighting element within it. The lighting element includes a luminous material that is self-illuminated, without the need for an external power source connected to the lighting element. Embodiments of the luminous material may include, but is not limited to, one or more of Dimethyl Phthalate, 2-Dipropylene Glycol Dimethyl Ether, and Hydrogen Peroxide. It should be noted that any suitable luminous material may be used as long as it achieves the objectives of the present specification.

The lighting element is used to provide light for viewing the sample collected on the filter. In alternate embodiments, the receiving structure is positioned inside and/or outside the main chamber 901. In some embodiments, the receiving structure is positioned above and/or below the filter. In various embodiments, the receiving structure is configured anywhere so that a lighting element placed within the receiving structure is capable of illuminating the sample collected on the filter. In embodiments where the receiving structure is positioned above the filter, the structure is configured to focus light on the sample while blocking light in other directions. In an embodiment, where a filter is positioned on a first side of the receiving structure in which the lighting element is placed, and a user views a sample placed in the filter through an endoscope for example, from the second side opposite to the first side, of the receiving structure; the surface of the receiving structure that is above the lighting element is blocked or configured to be opaque, so that only the first side of the receiving structure enables light from the lighting element to reflect on the specimen placed in a filter. Blocking one side of the receiving structure enables the light to be focused on the sample and avoids the possibility of a glare in the endoscopic vision.

In an embodiment, a portion of the receiving structure 902 is cylindrical in shape and comprises an internal hollow cylindrical space for receiving a cylindrically shaped stick filled with luminescent material (glow-stick). In different embodiments, the receiving structure 902 is hollow and shaped in the form of either a cylinder, a cuboid, a triangular prism, or any other shape so as to achieve the objectives of the present specification. In an embodiment, as shown in FIG. 9A, a front circular end of the receiving structure 902 is open and may be used for insertion of a cylindrically shaped container comprising a luminescent material to be placed within the internal hollow cylindrical space of the structure 902. In different embodiments, an opposing circular end (distal to the front end) of the receiving structure 902 may be open, rounded and closed, or flush with an internal back wall of the main chamber 901. In other embodiments, the receiving structure 902 may be of any shape and may receive a correspondingly shaped container comprising a luminescent material. In embodiments, the shape of the receiving structure 902 is designed such that a container containing the luminescent material can be inserted into said receiving structure such that it mates with and can be snapped into place into said receiving structure 902.

It should be appreciated that the volume of luminescent material is important. A small amount would result in an effective illumination of the area of interest. Too large an amount would be unnecessary, bulky, and possibly interfere with the filtering process. In one embodiment, the volume of luminescent material ranges from 10 $mm^3$ to 10000 $mm^3$ and may be incorporated into a container having any geometrical shape, including cylindrical (as described above), triangular, rectangular, spherical or other polygonal shapes. In embodiments, the volume of the luminescent material depends on the size of the main chamber of the biological sample catching device. For example, a larger device is equipped with a larger volume of the luminescent material.

Figure 9D:
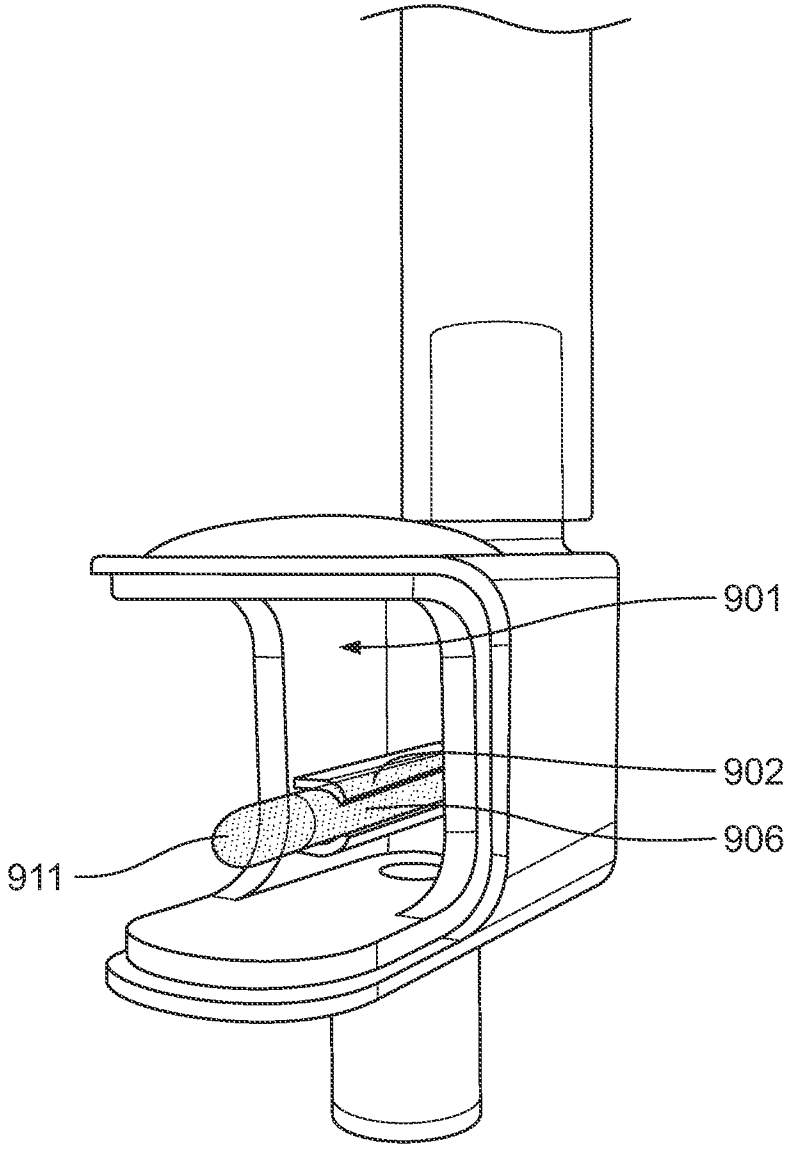
FIG. 9D illustrates a container comprising a disposable luminescent material placed within the receiving structure shown in FIG. 9A, in accordance with an embodiment of the present specification.
Figure 9E:
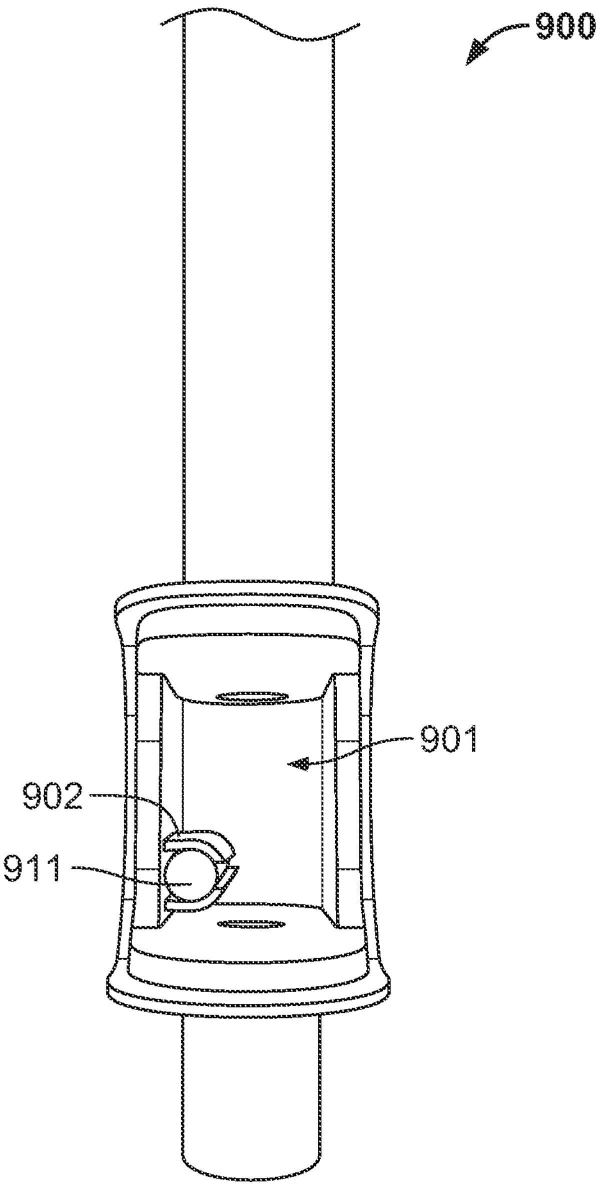
FIG. 9E illustrates a front view of the container comprising a disposable luminescent material placed within the receiving structure shown in FIG. 9A, in accordance with an embodiment of the present specification.
Figure 9F:
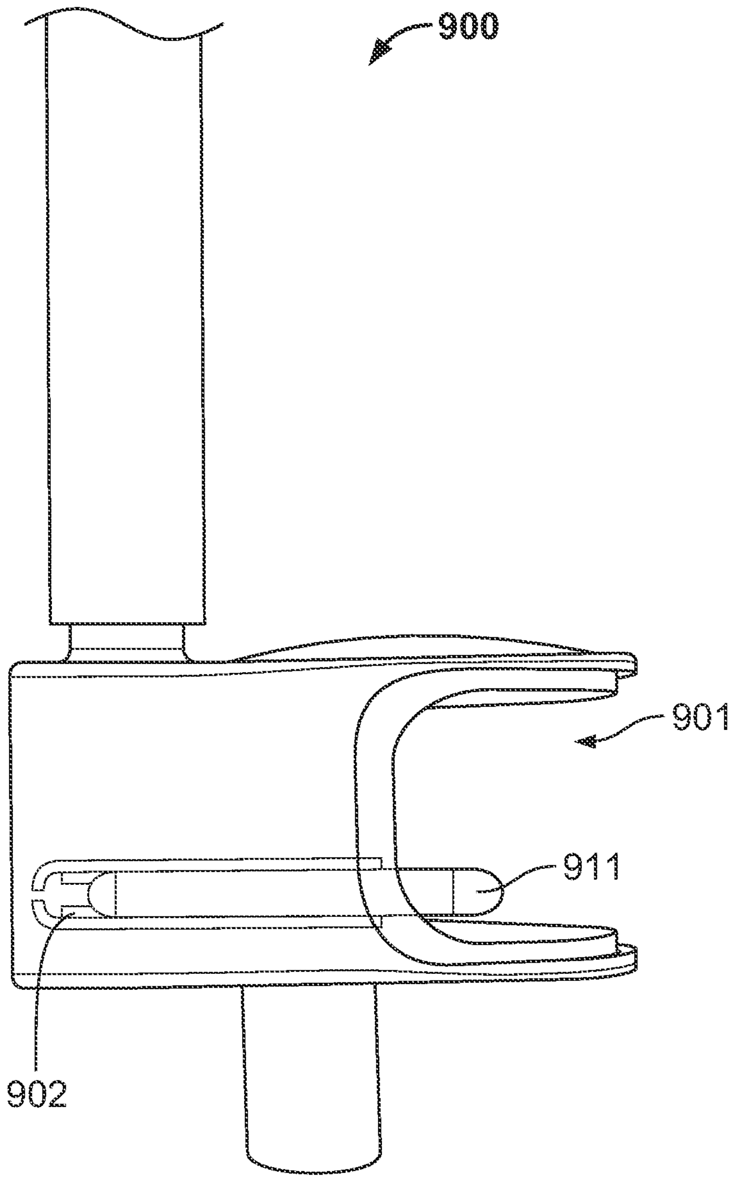
FIG. 9F illustrates a side view of the container comprising a disposable luminescent material placed in the receiving structure shown in FIG. 9A, in accordance with an embodiment of the present specification.
Figure 9G:
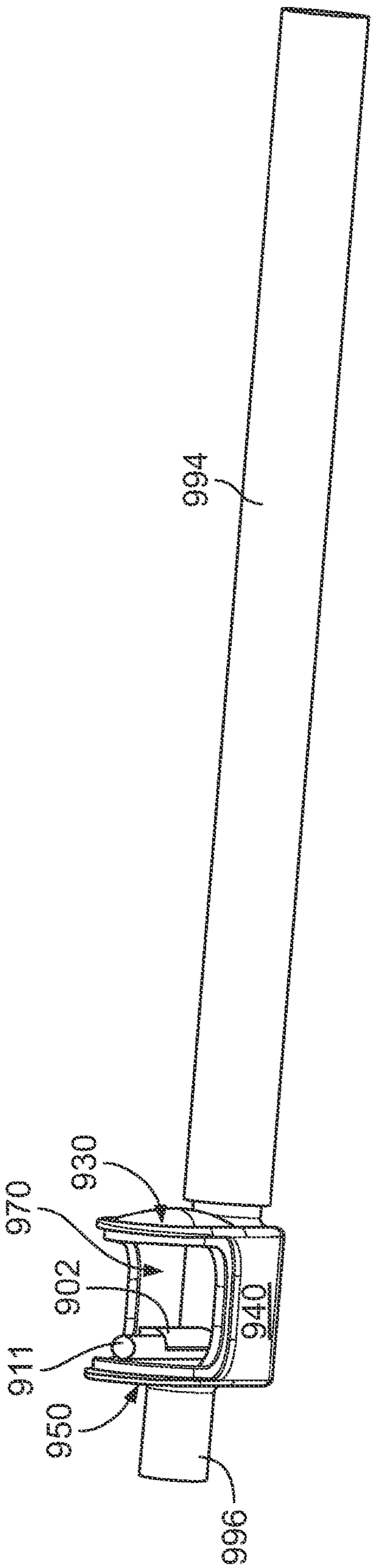
FIG. 9G is a side perspective view of the container comprising a luminescent or glow material placed within the receiving structure shown in FIG. 9A, in accordance with an embodiment of the present specification.
Figure 9H:
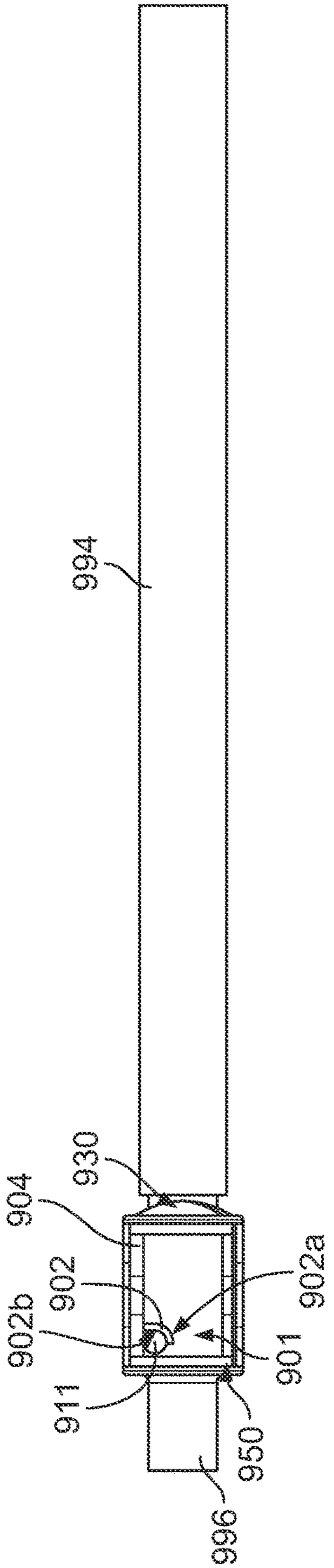
FIG. 9H is a side view from the aperture side of the container comprising a luminescent or glow material placed in the receiving structure shown in FIG. 9A, in accordance with an embodiment of the present specification.

FIG. 9D illustrates a container comprising a luminescent material 911 placed in the receiving structure 902 shown in FIG. 9A, in accordance with an embodiment of the present specification. FIG. 9E illustrates a front view of the container comprising a luminescent material 911 placed in the receiving structure 902 shown in FIG. 9A, in accordance with an embodiment of the present specification. FIG. 9F illustrates a side view of the container comprising a luminescent 911 or glow material placed in the receiving structure 902 shown in FIG. 9A, in accordance with an embodiment of the present specification. FIG. 9G is a side perspective view of the container comprising a luminescent or glow material 911 placed within the receiving structure 902 shown in FIG. 9A, in accordance with an embodiment of the present specification. FIG. 9H illustrates another side view from the aperture side 970 of the container comprising a luminescent or glow material 911 placed in the receiving structure 902 shown in FIG. 9A, in accordance with an embodiment of the present specification. Referring to FIGS. 9A-9H, a container 911 comprising a luminescent material having dimensions in order to fit within the hollow opening/slot 906 inside of the receiving structure 902 is placed within the internal hollow cylindrical space 906 of the receiving structure 902. In embodiments, any type of luminescent material filled in a container that mates with the receiving structure 902 may be used. In an embodiment, the container 911 comprising a luminescent material may be inserted within the receiving structure 902 via the opening/slot 906. In another embodiment, container 911 comprising a luminescent material may be inserted within the receiving structure 902 through the front circular open end. The position of the lighting element of container 911, owing to the position of receiving structure 902, is such that it does not interfere with the insertion of the removable filter.

Figure 10C:
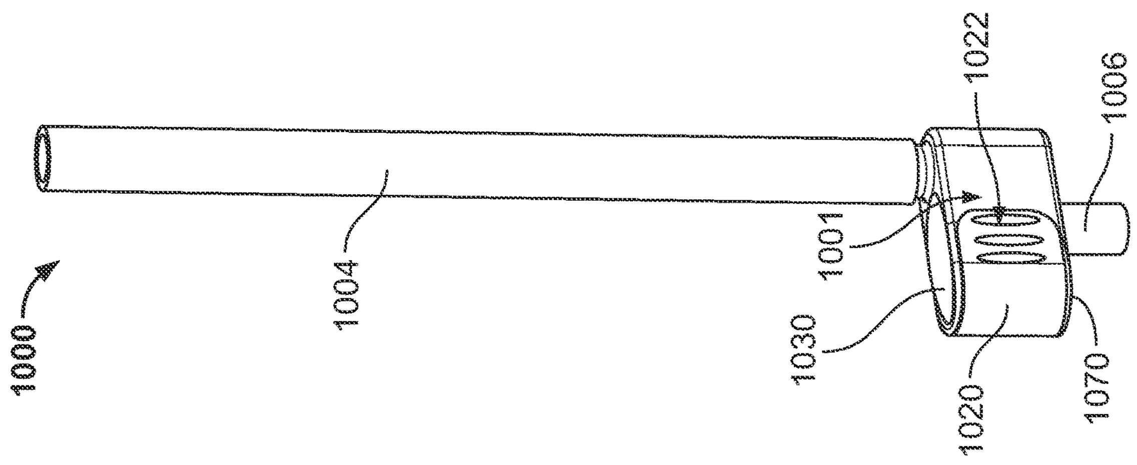
FIG. 10C illustrates a second elongated side perspective view of the biological specimen receiving device with specimen shelf, in accordance with some embodiments of the present specification.
Figure 10B:
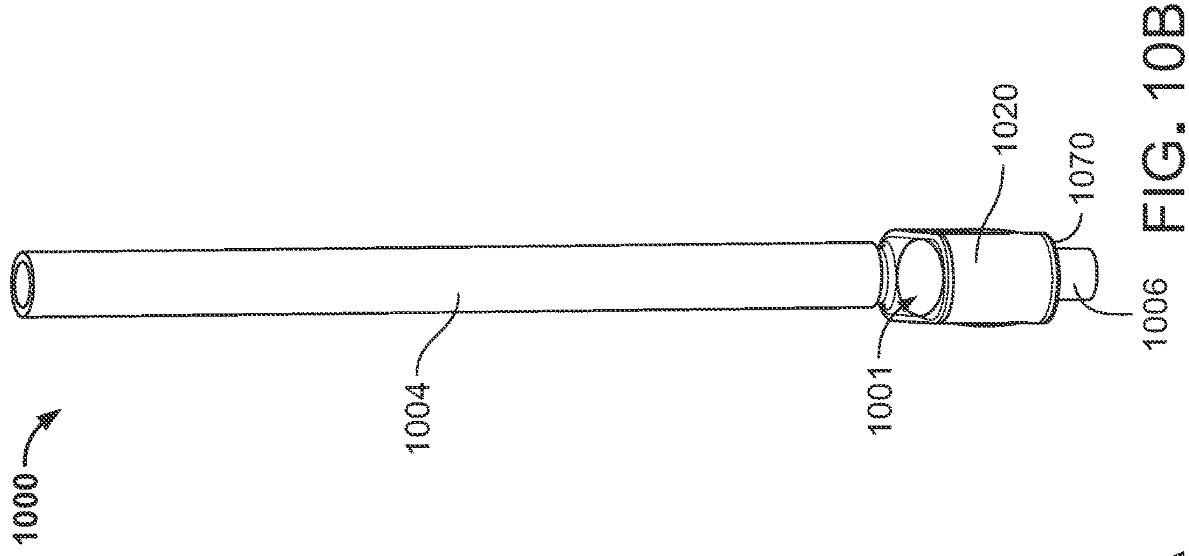
FIG. 10B illustrates an elongated front view of the biological specimen receiving device with specimen shelf, in accordance with some embodiments of the present specification.
Figure 10A:
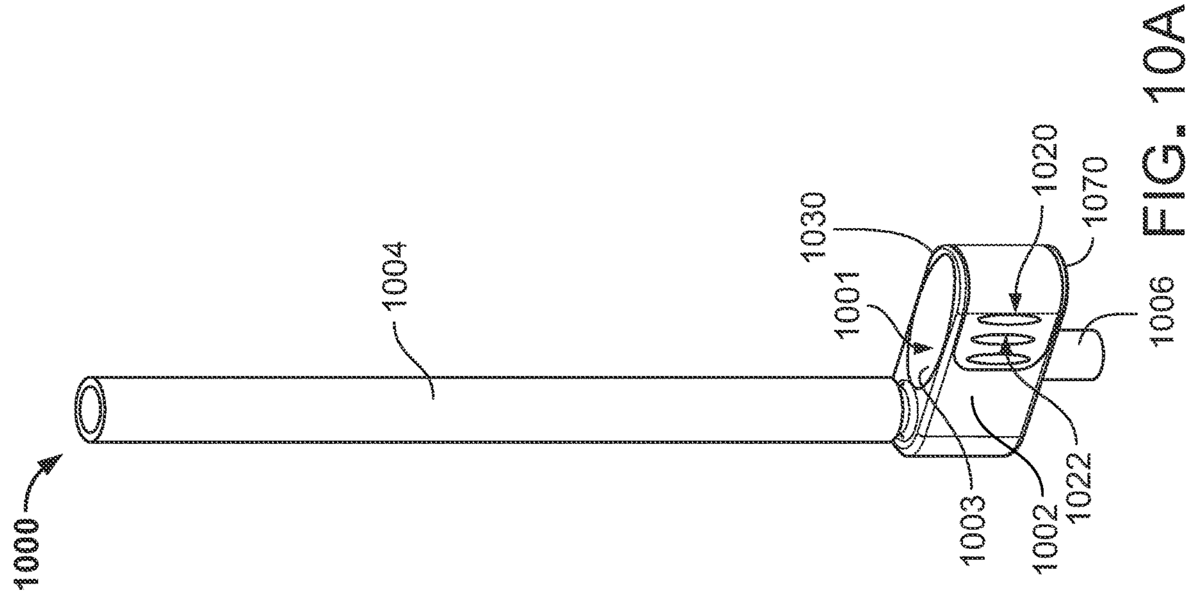
FIG. 10A illustrates a first elongated side perspective view of the biological specimen receiving device with specimen shelf, in accordance with some embodiments of the present specification.

FIGS. 10A to 10C illustrate different views of the specimen container 900 of FIGS. 9A to 9F, including a specimen shelf 1020 (also shown as specimen shelf 510 of FIG. 3), in accordance with some embodiments of the present specification. FIG. 10A illustrates a first elongated side perspective view of the biological specimen receiving device 1000 with specimen shelf 1020. FIG. 10B illustrates an elongated front view of the biological specimen receiving device 1000 with specimen shelf 1020. FIG. 10C illustrates a second elongated side perspective view of the biological specimen receiving device 1000 with specimen shelf 1020. Referring simultaneously to FIGS. 10A, 10B, and 10C, all the components including a receiving structure 1002, a main chamber 1001, an inlet 1004, and an outlet 1006, are identical to the corresponding components described in FIGS. 9A to 9F. Details of these components are not repeated here for brevity. In embodiments, the specimen shelf 1020 is removable and can be slid and/or is friction-fit between side portions 930 and 970. In some embodiments, a top surface of the main chamber 1001 is configured with a magnifying lens 1003 to provide an additional optical access to view a collected sample.

Specimen shelf 1020 is configured to cover the open side of the main chamber 1001, in between the inlet 1004 and the outlet 1006, and further in between the side portions 1030 and 1070. A surface of specimen shelf 1020 curves along and extends between the edges of side portions 1030 and 1070. Specimen shelf 1020 is configured to be inserted and removably retained at a side of the aperture between the side portions 1030 and 1070 of the main chamber 1001, thereby creating a seal. A friction grip 1022 is configured on both sides of the external curved surface of component 1020, to provide an ergonomic grip to a user to hold and attach or detach the specimen shelf 1020 from the main chamber 1001.

Figure 11B:
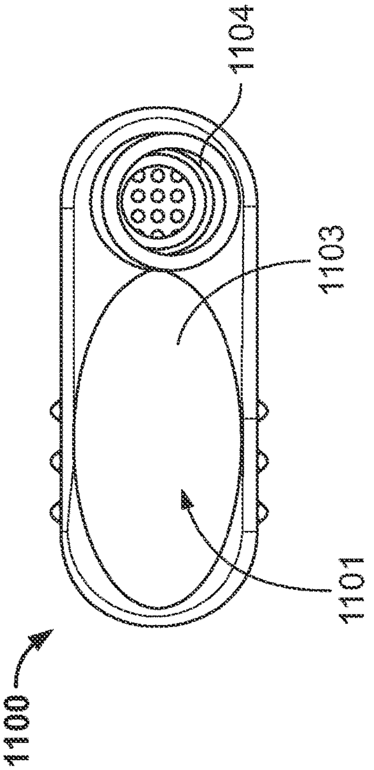
FIG. 11B illustrates a top-down view of the biological specimen receiving device of FIGS. 9A to 9F and FIGS. 10A to 10C, in accordance with embodiments of the present specification.
Figure 11C:
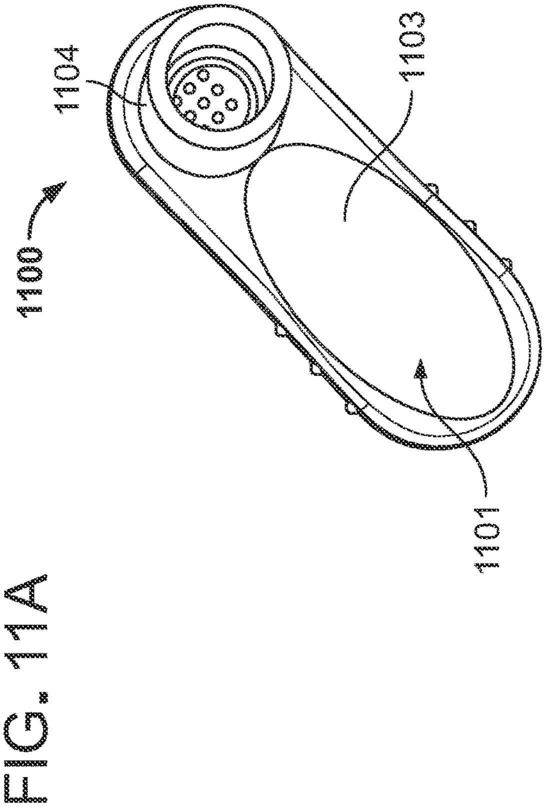
FIG. 11C illustrates a top-down perspective view of the biological specimen receiving device of FIGS. 9A to 9F and FIGS. 10A to 10C, in accordance with embodiments of the present specification.
Figure 11A:
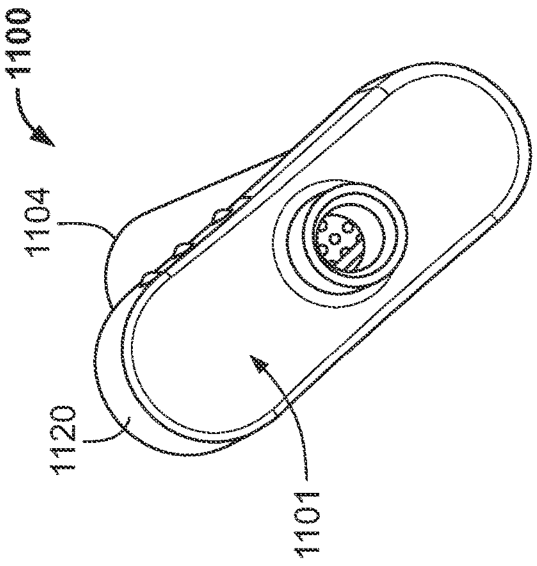
FIG. 11A illustrates a bottom-up view of the biological specimen receiving device of FIGS. 9A to 9F and FIGS. 10A to 10C, in accordance with embodiments of the present specification.

FIG. 11A illustrates a bottom-up view of the specimen container 900 and 1000 of FIGS. 9A to 9F and FIGS. 10A to 10C, in accordance with embodiments of the present specification. FIG. 11B illustrates a top-down view of the specimen container 900 and 1000 of FIGS. 9A to 9F and FIGS. 10A to 10C, in accordance with embodiments of the present specification. FIG. 11C illustrates a top-down perspective view of the specimen container 900 and 1000 of FIGS. 9A to 9F and FIGS. 10A to 10C, in accordance with embodiments of the present specification.

Figure 12:
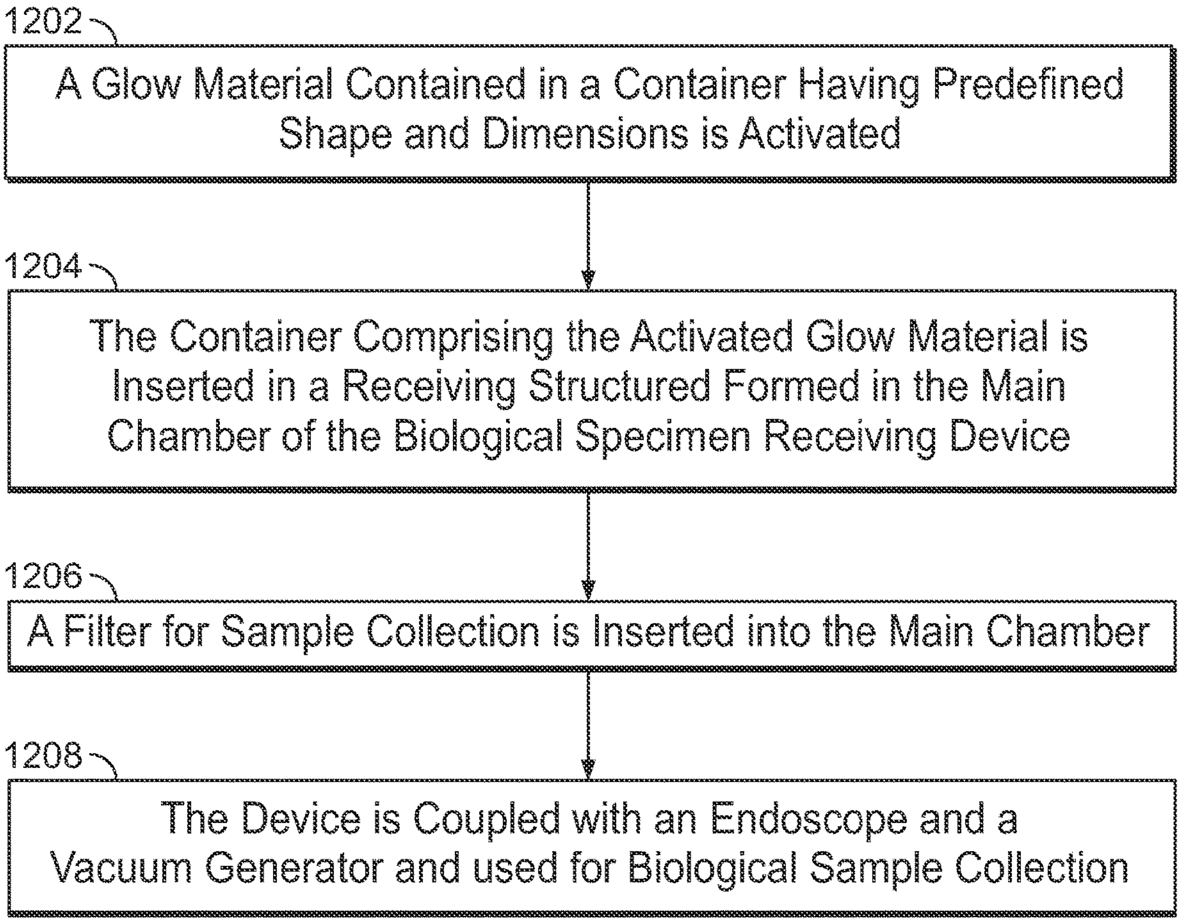
FIG. 12 is a flowchart illustrating a method of illuminating a main chamber of a biological specimen receiving device, in accordance with an embodiment of the present specification.

FIG. 12 is a flowchart illustrating a method of illuminating a main chamber of a biological specimen receiving device, in accordance with an embodiment of the present specification. At step 1202, a light emitting body contained in a container having predefined shape and dimensions is activated. In embodiments, the light emitting body is a luminescent material which is in the form of a light emitting diode (LED) or a glow stick and may be activated such that it emits light by using any of the known methods of activating a circuit or activating glow sticks, such as but not limited to, shaking the stick vigorously to mix fluidic chemicals contained in the stick or snapping the stick, breaking a seal, or pressing on the luminescent material container in a predefined way, wherein a chemical mixture formed by virtue of the physical manipulation of the container, emits light. In other embodiments, various other methods may be employed to activate different types of luminescent materials.

At step 1204 the container comprising the activated luminescent material is inserted into a receiving structure formed in the main chamber of the biological specimen receiving device as described above. In an embodiment, the receiving structure has a cylindrical shape and is coupled with a side internal wall of the device, as described with reference to FIGS. 9A-9D above. In an embodiment the container comprising the luminescent material is also cylindrically shaped and designed to fit in the cylindrically shaped receiving structure. In other embodiments, different shapes of receiving structures may be employed and the structure may be coupled with different portions of the internal walls of the main chamber of the device.

At step 1206 a filter for sample collection is inserted into the main chamber. At step 1208 the device is coupled with an endoscope and a vacuum generator such that it can be used for biological sample collection as described with reference to FIGS. 1-7 above.

The specimen container comprises a light emitting body/luminescent material, or glow material that may be placed within its receiving structure to illuminate an internal chamber or volume of the device, thereby enabling a specimen placed in a filter, as described above, in the main chamber to be clearly seen using an endoscopic device. The luminescent material is chosen to meet biological safety and/or regulatory requirements. Additionally, the dimensions and volume of the luminescent material are adjusted to the dimensions of the specimen container such that the luminescent material is neither too small relative to volume of the internal chamber, nor too big. In embodiments, the luminescent material has a volume ranging from 200 cubic millimeters ($mm^3$) to 600 $mm^3$. In one embodiment, the luminescent material has a volume of 283 cubic millimeter ($mm^3$). In another embodiment, the luminescent material has a volume of 500 $mm^3$. A relatively small volume of the luminescent material compared to the internal chamber volume may result in the light emitted by the material being insufficient to illuminate the biological sample. On the other hand, a relatively large volume of the luminescent material within the internal chamber, may result in an obstacle in the flow path between the inlet and the outlet at the top and bottom portions of the container. Thus, the volume of the luminescent material is, in one embodiment, a function of the internal volume of the space. Accordingly, if the internal volume is 6000 $mm^3$ to 120000 $mm^3$ (or any numerical increment therein), the volume of luminescent material may be linearly scaled in a range of 140 $mm^3$ to 2800 $mm^3$ (or any numerical increment therein).

Figure 13A:
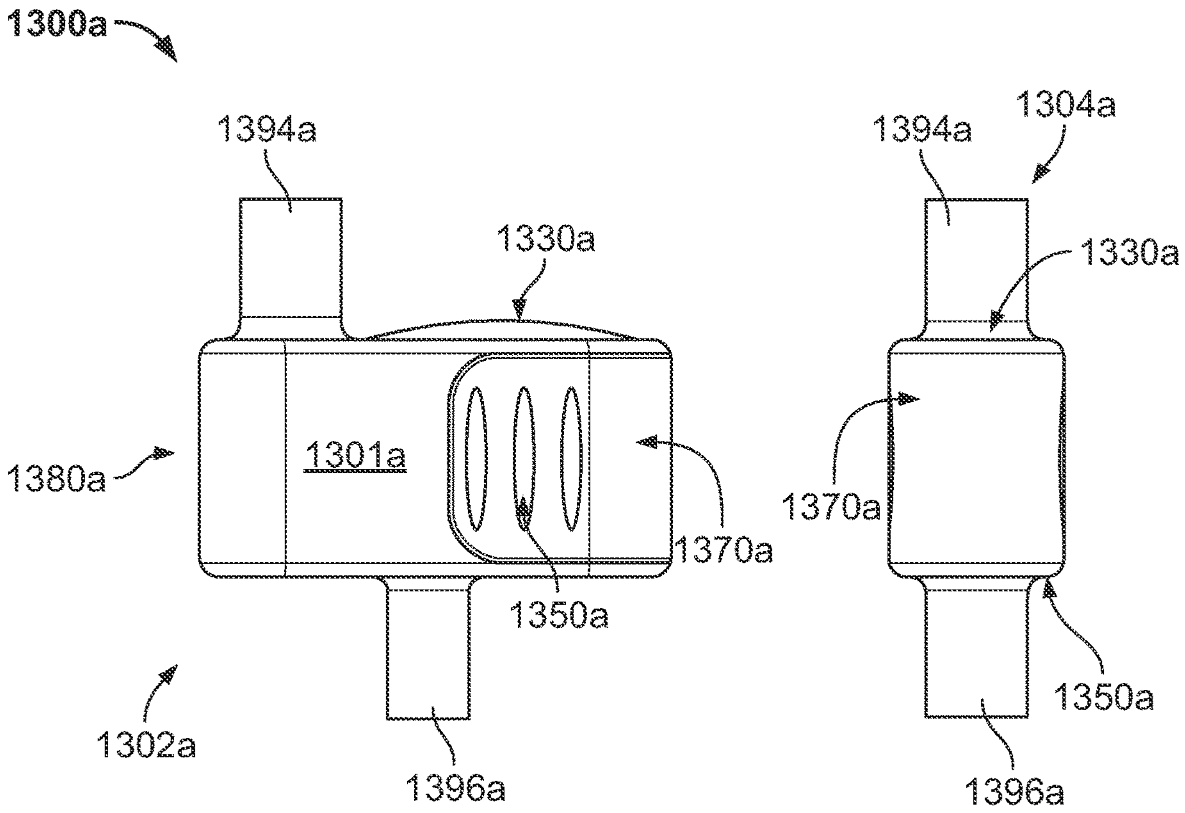
FIG. 13A is a side view and front view illustration of an embodiment of a specimen container as used in the present specification.

FIG. 13A is a side view 1302*a* and a front view 1304*a* illustration of a specimen container 1300*a*, showing exemplary dimensions, in accordance with some embodiments of the present specification. The various components of the container 1300*a* are similar to those already described above in context of FIGS. 1-7, and FIGS. 9A-9H, and are therefore not repeated here for brevity. The main chamber 1301*a* extends longitudinally between top portion 1330*a* and bottom portion 1350*a* and has a length or height of approximately 20 millimeters (mm); and latitudinally between an aperture side portion 1370*a* and an opposing non-aperture side portion 1380*a* and has a width of approximately 40 mm. A depth or thickness between two parallel walls that lie between the top portion 1330*a* and bottom portion 1350*a*, and between aperture side 1370*a* and opposing non-aperture side 1380*a*, is approximately 15 mm. In embodiments, inlet 1394*a* is oriented on and perpendicular to the surface of the top portion 1330*a* of the main chamber 1301*a* of the specimen container 1300*a*. The outlet 1396*a* is oriented on and perpendicular to the bottom portion 1350*a* of the main chamber 1301*a* of the specimen container 1300*a*.

Figure 13B:
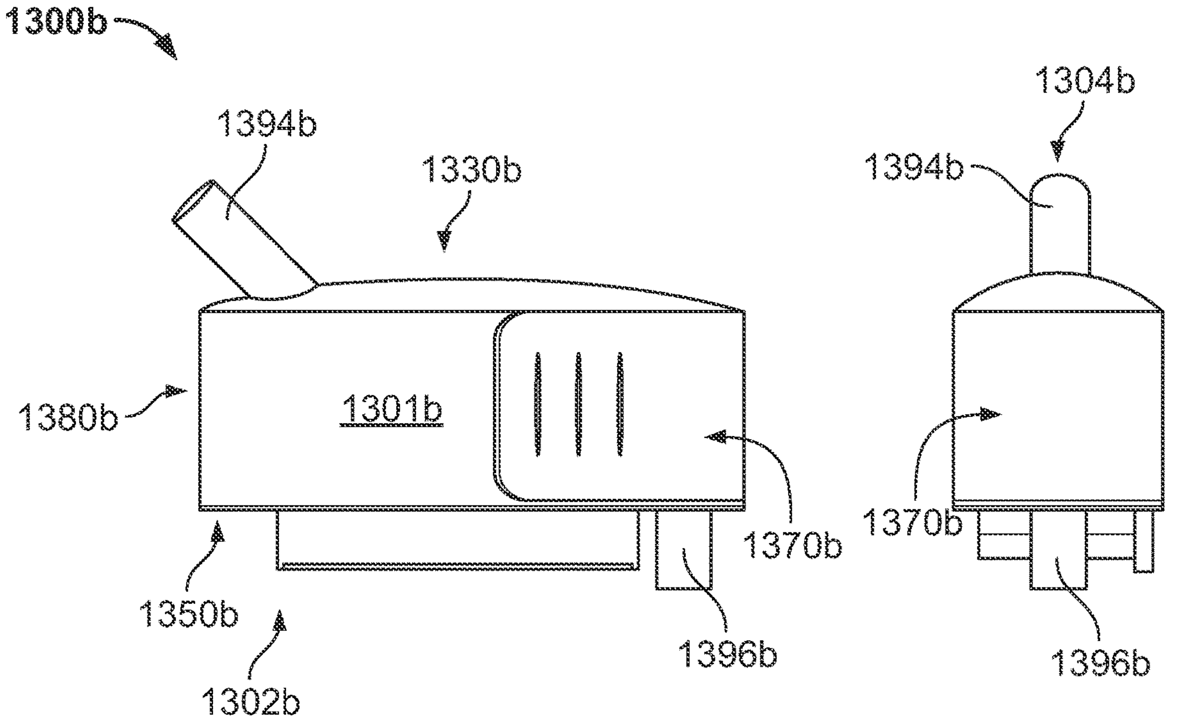
FIG. 13B is a side view and front view illustration of an embodiment of a specimen container as used in the present specification.

FIG. 13B illustrates a side view 1302*b* and a front view 1304*b*, with exemplary dimensions, of another specimen container 1300*b*, in accordance with some embodiments of the present specification. The various components of the container 1300*b* are similar to those already described above in context of FIGS. 1-7, and 9A-9H, and are therefore not repeated here for brevity. The main chamber 1301*b* extends longitudinally between top portion 1330*b* and bottom portion 1350*b* and has a length or height of approximately 30 mm; and latitudinally between an aperture side portion 1370*b* and an opposing non-aperture side portion 1380*b* and has a width of approximately 80 mm. A depth or thickness between two parallel walls that lie between the top portion 1330*b* and bottom portion 1350*b*, and between aperture side 1370*b* and opposing non-aperture side 1380*b*, is approximately 30 mm. In embodiments, inlet 1394*b* is oriented on and at an angle to the surface of the top portion 1330*b* of the main chamber 1301*b* of the specimen container 1300*b*. In one embodiment, the inlet 1394*b* forms an angle of approximately 45 degrees with the surface of the top portion 1330*b*.

The outlet 1396*b* is oriented on and perpendicular to the bottom portion 1350*b* of the main chamber 1301*b* of the specimen container 1300*b*.

Figure 13D:
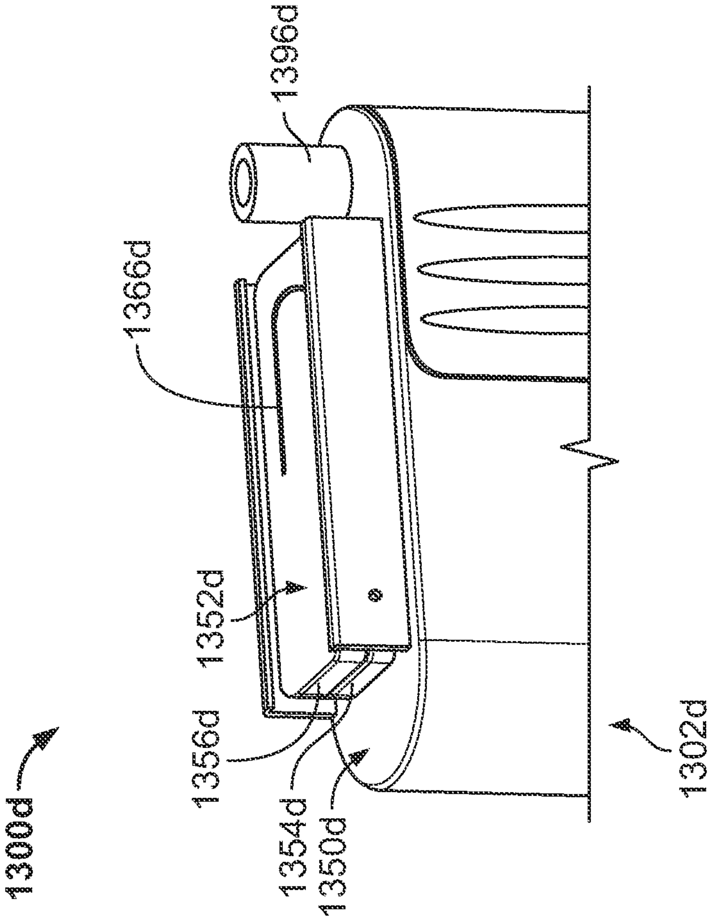
FIG. 13D is a bottom view of a specimen container, in accordance with some alternative embodiments of the present specification.
Figure 13C:
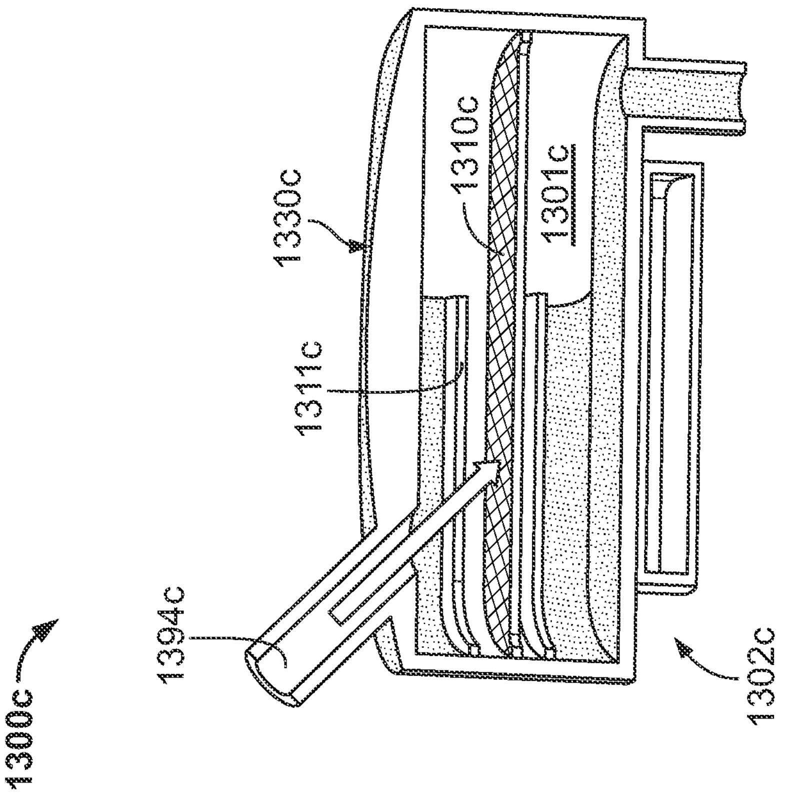
FIG. 13C is a cross-sectional illustration of the side view shown in FIG. 13B.

FIG. 13C is a cross-sectional illustration 1302*c* of side view 1302*b* shown in FIG. 13B. The figure shows a flow path from inlet 1394*c* at an angle of approximately 45 degrees, into the main chamber 1301*c*. During operation of the specimen container 1300*c*, a biological specimen is suctioned through inlet 1394*c* so that it glides smoothly through inlet 1394*c* and lands on a specimen shelf 1310*c* within the main chamber 1301*c*. A lighting element (or a light emitting element) 1311*c* is positioned proximate to the top portion 1394*c* in the interior of main chamber 1301*c*, which may illuminate the sample on shelf 1310*c*.

FIG. 13D illustrates a bottom view of 1302*d* of a specimen container 1300*d*, in accordance with some alternative embodiments of the present specification. The bottom view 1302*d* shows a bottom surface 1350*d* of a main chamber of the container 1300*d*. A portion of the bottom surface 1350*d* is attached to a rectangular chamber or compartment 1352*d* adjacent to an outlet 1396*d*. The additional chamber or compartment 1352*d* houses an LED lamp or any other form of a light emitting source that enables lighting a sample collected in the main chamber of container 1300*d* from a bottom side. In some embodiments, chamber 1352*d* includes two connected identically shaped housings 1354*d* and 1356*d*. The LED lamp is placed within chamber 1352*d* formed by the housings (covers) 1354*d* and 1356*d*. Upper housing 1354*d* is proximate to the main chamber of container 1300*d*, with an internal surface that houses the LED lamp within main chamber 1352*d*, and an external surface that is opposite to the inner surface of chamber 1352*d*. Lower housing 1356*d* covers the internal volume of upper housing 1354*d*. In some embodiments, an outer surface at the bottom of lower housing 1356*d* includes a button 1366*d*. In embodiments, button 1366*d* is a press button that is used to activate and deactivate the LED lamp within the housing formed by 1354*d* and 1356*d*.

Figure 13F:
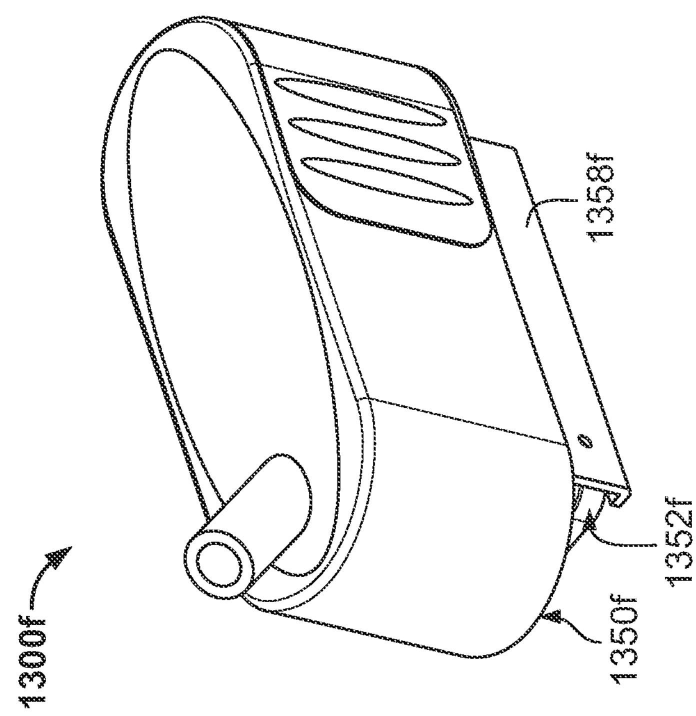
FIG. 13F is a top side perspective view of the specimen container as shown in FIG. 13D, in accordance with some embodiments of the present specification.
Figure 13E:
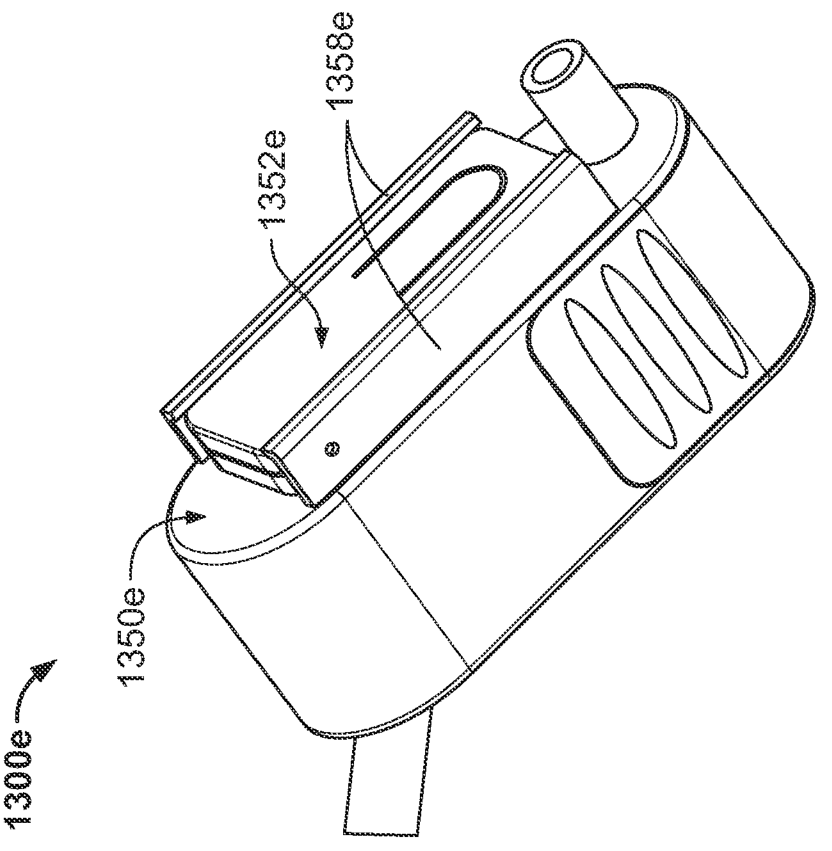
FIG. 13E is a bottom side perspective view of the specimen container shown in FIG. 13D, in accordance with some embodiments of the present specification.

FIG. 13E is a bottom side perspective view of the specimen container 1300*d* of FIG. 13D, in accordance with some embodiments of the present specification. FIG. 13F is a top side perspective view of the specimen container 1300*d* of FIG. 13D, in accordance with some embodiments of the present specification. It should be noted that embodiments and dimensions described in FIGS. 13A to 13F are exemplary only, and other dimensions of the specimen container are also possible within the scope of the described specification. Referring to FIGS. 13E and 13F, a channel 1358*e*/1358*f* is provided on a bottom surface 1350*e*/1350*f* of a container 1300*e*/1300*f*, comprising two parallel walls that are configured to receive the chamber 1352*e*/1352*f*. Therefore, chamber 1352*e*/1352*f* is removable connected to bottom surface 1350*e*/1350*f* of the container 1300*e*/1300*f*. In some embodiments, LED lamp is inserted directly into the channel 1358*e*/1358*f* without chamber 1352*d*.

Figure 13G:
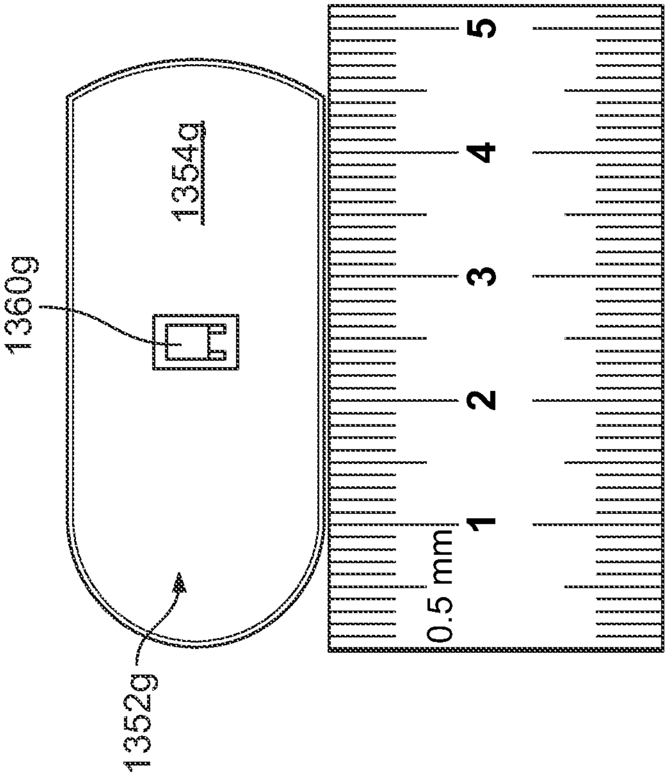
FIG. 13G is a photograph of an exemplary specimen container described in accordance with embodiments of the present specification; and, FIG. 13H is a photograph of an exemplary specimen container described in accordance with embodiments of the present specification.
Figure 13H:
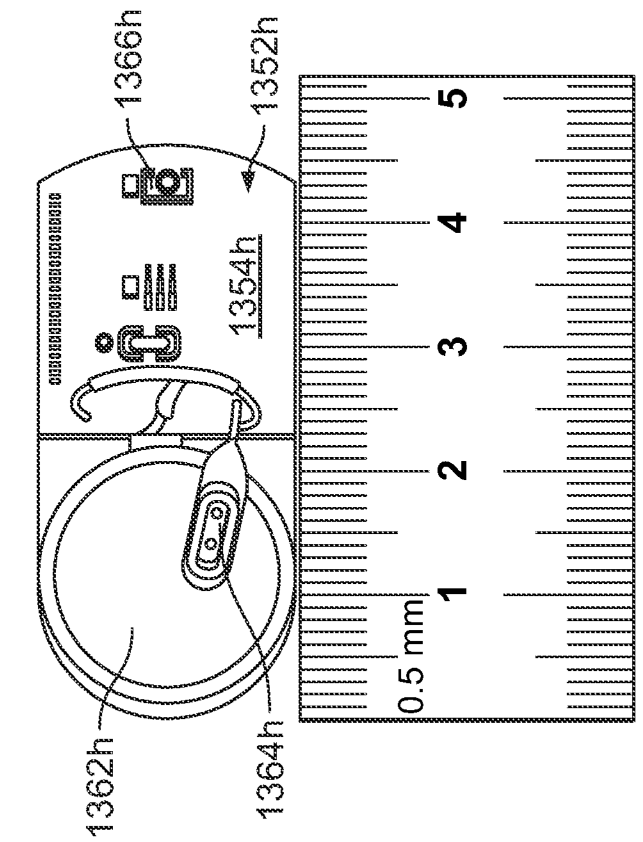

FIG. 13G illustrates an LED lamp 1360*g* positioned on an outer surface of upper housing 1354*d* of FIG. 13D, and therefore on the external surface of chamber 1352*d* adjacent to bottom surface 1350*d* of main chamber of the container 1300*d*. FIG. 13H illustrates components configured on an internal surface of upper housing 1354*d*, inside chamber 1352*d*, and opposite to the surface holding LED lamp 1360*g* of FIG. 13G. The internal surface of upper housing 1354*h* includes a battery 1362*h* that is attached to an electrode 1364*h*. The LED lamp 1360*g* is connected to the electrode 1364*h* through the surface of housing 1354*h*. The battery 1362*h* is configured to power the LED lamp 1360*g*. Operation of the lamp 1360*g* is controlled with a button or switch 1366*h*, which is activated through an interface provided on the external surface of lower housing 1356*d* or bottom of chamber 1352*h*. The surface of housing 1354*g*/chamber 1354*h* is approximately 2.5 to 5 centimeter (cm) wide.

Having thus described illustrative embodiments of the present invention, those skilled in the art will appreciate that the disclosures are illustrative only and that various other alternatives, adaptations, and modifications may be made within the scope of the present invention. Accordingly, the present invention is not limited to the specific embodiments as illustrated herein, but is only limited by the following claims.

We claim:

1. A device configured to catch a biological specimen removed from an individual, the device comprising at least:

an inlet channel having a first central axis;

an outlet channel having a second central axis, wherein the second central axis is offset from the first central axis;

a filter defining a filter path;

a main chamber having an interior wall and an exterior wall, wherein the main chamber is in fluid communication with the inlet channel, is in fluid communication with the outlet channel, and is configured to receive the filter, whereby the inlet channel, main chamber, and outlet channel form a fluid flow channel; and a receiving structure attached to at least a portion of the interior wall or the exterior wall of the main chamber and positioned such that the receiving structure does not obstruct either the inlet channel or the outlet channel, wherein the receiving structure comprises a hollow lumen having a first wall positioned flush against the interior wall of the main chamber and a second opposing wall defining an elongated opening sized to removably receive a light-emitting body, is configured so as to avoid obstruction of the filter path, is configured to illuminate the main chamber when the light-emitting body is inserted, and is located relative to the fluid flow channel such that illumination occurs without the light-emitting body contacting the specimen.

2. The device of claim 1 wherein the light emitting body comprises a container with a light emitting material, wherein the container is adapted to be positioned within the receiving structure and configured to illuminate the main chamber.

3. The device of claim 1 wherein the light emitting body comprises a circuit and light emitting diode (LED), wherein the circuit and LED is configured to be positioned within the receiving structure and configured to illuminate the main chamber.

4. The device of claim 1 wherein the interior wall is at least partially curved.

5. The device of claim 1 wherein the main chamber comprises a transparent material.

6. The device of claim 1 wherein the receiving structure comprises a transparent material.

7. The device of claim 2 wherein the receiving structure is cylindrical.

8. The device of claim 2, wherein the container comprising the light emitting material is a structure that is one of cylindrical, cuboidal, and triangular prism.

9. The device of claim 1 wherein the receiving structure is made from clear plastic.

10. The device of claim 1 wherein a volume of the light emitting body is in a range one of 10 cubic millimeter ($mm^3$) to 10000 $mm^3$.

11. The device of claim 1 wherein the light emitting body is adapted to be activated such that the light emitting body emits light before the light emitting body is received into the receiving structure.

12. A method of illuminating a main chamber of a device configured to catch a biological specimen removed from an individual, the main chamber having an interior wall and an exterior wall, wherein the device comprises an inlet in fluid communication with the main chamber, a filter defining a filter path and configured to be removably inserted into the main chamber, and an outlet in fluid communication with the main chamber, wherein the inlet, main chamber, and outlet form a fluid flow channel the method comprising:

obtaining a volume of a light emitting material in a container, activating the light emitting material to emit light; and placing the container in a receiving structure before catching the biological specimen removed from an individual, wherein the receiving structure is attached to at least a portion of the interior wall or the exterior wall of the main chamber and positioned such that the receiving structure does not obstruct either the inlet channel or the outlet channel, wherein the receiving structure comprises a hollow lumen having a first wall positioned flush against the interior wall of the main chamber and a second opposing wall defining an elongated opening sized to removably receive the container, is configured so as to avoid obstruction of the inlet and outlet and the filter path, is configured to illuminate the main chamber when the container is inserted, and is located adjacent the filter and relative to the fluid flow channel such that illumination occurs without the light emitting material contacting the specimen.

13. The method of claim 12 further comprising inserting the filter into the main chamber, wherein the filter is adapted to collect the biological specimen.

14. The method of claim 12 further comprising coupling the device with an endoscope and a vacuum generator adapted to apply a suction to the device.

15. The method of claim 12 wherein the main chamber comprises a transparent material.

16. The method of claim 12 wherein the receiving structure comprises a transparent material.

17. The method of claim 12 wherein the receiving structure is cylindrical.

18. The method of claim 17 wherein the container is received into the receiving structure via the elongated opening on the second opposing side.

19. The method of claim 12 wherein the volume of the light emitting material is in a range of 10 $mm^3$ to 10000 $mm^3$.

* * * * *